(12) United States Patent
Small et al.

(10) Patent No.: US 9,937,156 B2
(45) Date of Patent: Apr. 10, 2018

(54) MODULATION OF MRTF-A ACTIVITY IN PATHOLOGIC FIBROSIS AND WOUND HEALING

(71) Applicant: The Board of Regents of the University of Texas System, Austin, TX (US)

(72) Inventors: Eric M. Small, Rochester, NY (US); Eric N. Olson, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/029,222

(22) PCT Filed: Oct. 16, 2014

(86) PCT No.: PCT/US2014/060904
§ 371 (c)(1),
(2) Date: Apr. 13, 2016

(87) PCT Pub. No.: WO2015/057964
PCT Pub. Date: Apr. 23, 2015

(65) Prior Publication Data
US 2016/0256441 A1 Sep. 8, 2016

Related U.S. Application Data

(60) Provisional application No. 61/891,693, filed on Oct. 16, 2013.

(51) Int. Cl.
| | | |
|---|---|---|
| *A61K 31/42* | (2006.01) | |
| *A61K 45/06* | (2006.01) | |
| *A61F 13/00* | (2006.01) | |
| *A61G 10/02* | (2006.01) | |
| *A61K 9/06* | (2006.01) | |
| *A61K 9/08* | (2006.01) | |
| *A61K 9/14* | (2006.01) | |
| *A61L 17/00* | (2006.01) | |
| *A61L 17/06* | (2006.01) | |
| *A61M 1/00* | (2006.01) | |
| *A61N 1/04* | (2006.01) | |
| *A61N 5/06* | (2006.01) | |
| *A61N 7/00* | (2006.01) | |
| *C07K 16/18* | (2006.01) | |
| *C12N 15/113* | (2010.01) | |
| *A61L 15/44* | (2006.01) | |
| *A61L 26/00* | (2006.01) | |

(52) U.S. Cl.
CPC ........ *A61K 31/42* (2013.01); *A61F 13/00021* (2013.01); *A61G 10/026* (2013.01); *A61K 9/06* (2013.01); *A61K 9/08* (2013.01); *A61K 9/14* (2013.01); *A61K 45/06* (2013.01); *A61L 15/44* (2013.01); *A61L 17/005* (2013.01); *A61L 17/06* (2013.01); *A61L 26/0066* (2013.01); *A61M 1/0088* (2013.01); *A61N 1/0468* (2013.01); *A61N 5/062* (2013.01); *A61N 7/00* (2013.01); *C07K 16/18* (2013.01); *C12N 15/113* (2013.01); *A61L 2300/204* (2013.01); *A61L 2300/412* (2013.01)

(58) Field of Classification Search
CPC .............................. A61K 31/42; C07D 261/20
USPC ......................................... 514/378, 379, 380
See application file for complete search history.

(56) References Cited

U.S. PATENT DOCUMENTS

| | | | |
|---|---|---|---|
| 2005/0249695 A1 | 11/2005 | Tiller et al. | |
| 2006/0217389 A1 | 9/2006 | Sun et al. | |
| 2007/0123503 A1 | 5/2007 | Malfroy-Camine et al. | |
| 2007/0134301 A1 | 6/2007 | Ylitalo et al. | |
| 2009/0042958 A1 | 2/2009 | Shaw | |
| 2009/0264443 A1 | 10/2009 | Helton et al. | |
| 2011/0082171 A1 | 4/2011 | Ferguson et al. | |
| 2012/0027875 A1 | 2/2012 | Melman | |
| 2012/0136323 A1 | 5/2012 | Stasko et al. | |
| 2014/0024690 A1* | 1/2014 | Abramite ............ | C07D 261/08 514/380 |

FOREIGN PATENT DOCUMENTS

EP   2 100 602   9/2009

OTHER PUBLICATIONS

Cao et al., "Modulation of smooth muscle gene expression by association of histone acetyltransferases and deacetylases with myocardin," Mol Cell Biol, 25(1):364-376, 2005.
Cen et al., "Myocardin/MKL family of SRF coactivators: key regulators of immediate early and muscle specific gene expression," J Cell Biochem, 93(1):74-82 2004.
Crider et al.,"Myocardin-related transcription factors A and B are key regulators of TGF-β1-induced fibroblast to myofibroblast differentiation," J. Invest Dermatol., 131(12):2378-2385, 2011.
Du et al.,"Myocardin is a critical serum response factor cofactor in the transcriptional program regulating smooth muscle cell differentiation," Mol Cell Biol, 23(7):2425-2437, 2003.
Elberg et al., "MKL1 mediates TGF-betal-induced alpha-smooth muscle actin expression in human renal epithelial cells," Am J Physiol Renal Physiol, 294(5):F1116-1128, 2008.
Fan et al., "Cell contact-dependent regulation of epithelial-myofibroblast transition via the rho-rho kinase-phospho-myosin pathway," Mol Biol Cell, 18(3):1083-1097, 2007.
Guettler et al., "RPEL motifs link the serum response factor cofactor MAL but not myocardin to Rho signaling via actin binding," Mol Cell Biol, 28(2):732-742, 2008.
Hamid et al., "Rho kinase activation plays a major role as a mediator of irreversible injury in reperfused myocardium," Am. J. Physiol. Heart Circ. Physiol., 292:H2598-H2606, 2007.
Hattori et al., "Long-term inhibition of Rho-kinase suppresses left ventricular remodeling after myocardial infarction in mice," Circulation, 109:2234-2239, 2004.
Haudek et al., "Rho kinase-1 mediates cardiac fibrosis by regulating fibroblast precursor cell differentiation," Cardiovasc Res., 83:511-518, 2009.

(Continued)

Primary Examiner — Raymond J Henley, III
(74) Attorney, Agent, or Firm — Parker Highlander PLLC

(57) ABSTRACT

The present disclosure concerns uses for isoxazole compounds or salts or analogs thereof for the treatment of wounds. The present disclosure also concerns devices for delivering a isoxazole compound or salts or an analogs thereof to a wound site.

28 Claims, 14 Drawing Sheets

(56) References Cited

OTHER PUBLICATIONS

Kuwahara et al., "Muscle-specific signaling mechanism that links actin dynamics to serum response factor," *Mol. Cell Biol.*, 25:3173-3181, 2005.

Li et al., "Requirement of a myocardin-related transcription factor for development of mammary myoepithelial cells," *Mol Cell Biol*, 26(15):5797-5808, 2006.

Miralles et al., "Actin dynamics control SRF activity by regulation of its coactivator MAL," *Cell*, 113(3):329-342, 2003.

Muehlich et al., "Serum-induced phosphorylation of the serum response factor coactivator MKL1 by the extracellular signal-regulated kinase 1/2 pathway inhibits its nuclear localization," *Mol Cell Biol*, 28(20):6302-6313, 2008.

Oh et al., "Requirement of myocardin-related transcription factor-B for remodeling of branchial arch arteries and smooth muscle differentiation," *Proc. Natl. Acad. Sci. USA*, 102:15122-15127, 2005.

Olson & Nordheim, "Linking actin dynamics and gene transcription to drive cellular motile functions," *Nat Rev Mol Cell Biol*, 11(5):353-365, 2010.

PCT International Preliminary Report on Patentability issued in International Application No. PCT/US2014/060904, dated Apr. 28, 2016.

PCT International Search Report and Written Opinion issued in International Application No. PCT/US2014/060904, dated Mar. 25, 2015.

Pipes et al., "The myocardin family of transcriptional coactivators: versatile regulators of cell growth, migration, and myogenesis," *Genes Dev.*, 20(12):1545-1556, 2006.

Rikitake et al., "Decreased perivascular fibrosis but not cardiac hypertrophy in ROCK1+/− haploinsufficient mice," *Circulation*, 112:2959-2965, 2005.

Russell et al., "Regulated expression of pH sensing G Protein-coupled receptor-68 identified through chemical biology defines a new drug target for ischemic heart disease," *ACS Chemical Biology*, 7(6):1077-1083, 2012.

Russell et al., "Targeting native adult heart progenitors with cardiogenic small molecules," *ACS Chemical Biology*, 7(6):1067-1076, 2012.

Schneider, et al., "Small-molecule activation of neuronal cell fate," *Nat Chem Biol*, 4(7):408-410, 2008.

Small et al., "Myocardin is sufficient and necessary for cardiac gene expression in Xenopus," *Development*, 132(5):987-997, 2005.

Small et al., "Myocardin-related transcription factor-A controls myofibroblast activation and fibrosis in response to myocardial infarction," *Circ Res.*, 107:294-304, 2010.

Sun et al., "Defining the mammalian CArGome," *Genome Res*, 16(2):197-207, 2006.

Velasquez et al., "Activation of MRTF-A-dependent gene expression with a small molecule promotes myofibroblast differentiation and wound healing," *PNAS*, 110(42):16850-16855, 2013.

Wang et al, "Potentiation of serum response factor activity by a family of myocardin-related transcription factors," *Proc Natl Acad Sci USA*, 99(23):14855-14860, 2002.

Wang et al., "Activation of cardiac gene expression by myocardin, a transcriptional cofactor for serum response factor," *Cell*, 105(7):851-862, 2001.

Wang et al., "Myocardin and ternary complex factors compete for SRF to control smooth muscle gene expression," *Nature*, 428(6979):185-189, 2004.

Zhang et al., "Targeted deletion of ROCK1 protects the heart against pressure overload by inhibiting reactive fibrosis," *FASEB J.*, 20:916-925, 2006.

Zhao et al., "Force activates smooth muscle alpha-actin promoter activity through the Rho signaling pathway," *J Cell Sci*, 120(Pt 10):1801-1809, 2007.

\* cited by examiner

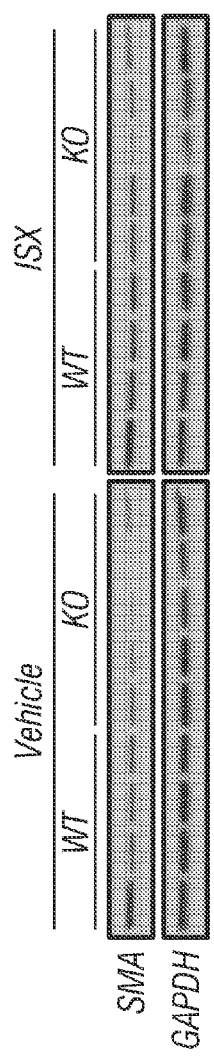
FIG. 4D
FIG. 4E
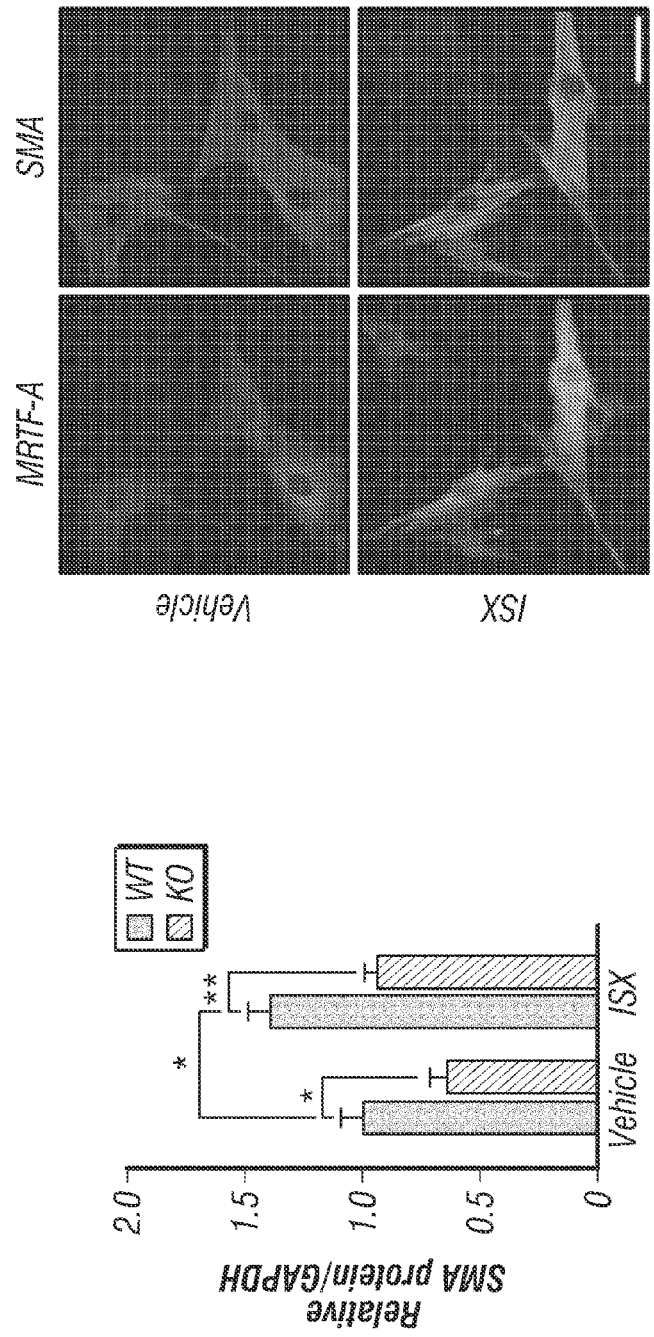
FIG. 5A

SEQUENCE LISTING

<160> NUMBER OF SEQ ID NOS: 26

<210> SEQ ID NO 1
<211> LENGTH: 20
<212> TYPE: DNA
<213> ORGANISM: Artificial
<220> FEATURE:
<223> OTHER INFORMATION: Synthetic oligonucleotide

<400> SEQUENCE: 1
taggccattg tgtatgcagc                                               20

<210> SEQ ID NO 2
<211> LENGTH: 21
<212> TYPE: DNA
<213> ORGANISM: Artificial
<220> FEATURE:
<223> OTHER INFORMATION: Synthetic oligonucleotide

<400> SEQUENCE: 2
acatgttcag ctttgtggac c                                             21

<210> SEQ ID NO 3
<211> LENGTH: 20
<212> TYPE: DNA
<213> ORGANISM: Artificial
<220> FEATURE:
<223> OTHER INFORMATION: Synthetic oligonucleotide

<400> SEQUENCE: 3
agcaggtcct tggaaacctt                                               20

<210> SEQ ID NO 4
<211> LENGTH: 20
<212> TYPE: DNA
<213> ORGANISM: Artificial
<220> FEATURE:
<223> OTHER INFORMATION: Synthetic oligonucleotide

<400> SEQUENCE: 4
aaggagtttc atctggccct                                               20

<210> SEQ ID NO 5
<211> LENGTH: 20
<212> TYPE: DNA
<213> ORGANISM: Artificial
<220> FEATURE:
<223> OTHER INFORMATION: Synthetic oligonucleotide

<400> SEQUENCE: 5
taggactgac caaggtggct                                               20

<210> SEQ ID NO 6
<211> LENGTH: 21
<212> TYPE: DNA
<213> ORGANISM: Artificial
<220> FEATURE:
<223> OTHER INFORMATION: Synthetic oligonucleotide

<400> SEQUENCE: 6
ggaacctggt ttcttctcac c                                             21

<210> SEQ ID NO 7
<211> LENGTH: 18
<212> TYPE: DNA
<213> ORGANISM: Artificial

```
<220> FEATURE:
<223> OTHER INFORMATION: Synthetic oligonucleotide

<400> SEQUENCE: 7
cgtgccgcct ggagaaac                                                  18

<210> SEQ ID NO 8
<211> LENGTH: 21
<212> TYPE: DNA
<213> ORGANISM: Artificial
<220> FEATURE:
<223> OTHER INFORMATION: Synthetic oligonucleotide

<400> SEQUENCE: 8
tgggagttgc tgttgaagtc g                                              21

<210> SEQ ID NO 9
<211> LENGTH: 20
<212> TYPE: DNA
<213> ORGANISM: Artificial
<220> FEATURE:
<223> OTHER INFORMATION: Synthetic oligonucleotide

<400> SEQUENCE: 9
ctacaggctc cgagatgaac                                                20

<210> SEQ ID NO 10
<211> LENGTH: 22
<212> TYPE: DNA
<213> ORGANISM: Artificial
<220> FEATURE:
<223> OTHER INFORMATION: Synthetic oligonucleotide

<400> SEQUENCE: 10
ttcttctttg ggtattgctt gg                                             22

<210> SEQ ID NO 11
<211> LENGTH: 23
<212> TYPE: DNA
<213> ORGANISM: Artificial
<220> FEATURE:
<223> OTHER INFORMATION: Synthetic oligonucleotide

<400> SEQUENCE: 11
acaaagaaat gatggatgct acc                                            23

<210> SEQ ID NO 12
<211> LENGTH: 22
<212> TYPE: DNA
<213> ORGANISM: Artificial
<220> FEATURE:
<223> OTHER INFORMATION: Synthetic oligonucleotide

<400> SEQUENCE: 12
gtatctctct gaaggactct gg                                             22

<210> SEQ ID NO 13
<211> LENGTH: 19
<212> TYPE: DNA
<213> ORGANISM: Artificial
<220> FEATURE:
<223> OTHER INFORMATION: Synthetic oligonucleotide

<400> SEQUENCE: 13
acgaggcggt taccatcac                                                 19
```

```
<210> SEQ ID NO 14
<211> LENGTH: 20
<212> TYPE: DNA
<213> ORGANISM: Artificial
<220> FEATURE:
<223> OTHER INFORMATION: Synthetic oligonucleotide

<400> SEQUENCE: 14
gcagacagag acaggagcac                                               20

<210> SEQ ID NO 15
<211> LENGTH: 20
<212> TYPE: DNA
<213> ORGANISM: Artificial
<220> FEATURE:
<223> OTHER INFORMATION: Synthetic oligonucleotide

<400> SEQUENCE: 15
cgatagctcc aagaagcagc                                               20

<210> SEQ ID NO 16
<211> LENGTH: 20
<212> TYPE: DNA
<213> ORGANISM: Artificial
<220> FEATURE:
<223> OTHER INFORMATION: Synthetic oligonucleotide

<400> SEQUENCE: 16
ttttctggtt gcttccctca                                               20

<210> SEQ ID NO 17
<211> LENGTH: 20
<212> TYPE: DNA
<213> ORGANISM: Artificial
<220> FEATURE:
<223> OTHER INFORMATION: Synthetic oligonucleotide

<400> SEQUENCE: 17
aaggtccatt ccaactgctc                                               20

<210> SEQ ID NO 18
<211> LENGTH: 21
<212> TYPE: DNA
<213> ORGANISM: Artificial
<220> FEATURE:
<223> OTHER INFORMATION: Synthetic oligonucleotide

<400> SEQUENCE: 18
ccatctctac tgctgtcatc c                                             21

<210> SEQ ID NO 19
<211> LENGTH: 20
<212> TYPE: DNA
<213> ORGANISM: Artificial
<220> FEATURE:
<223> OTHER INFORMATION: Synthetic oligonucleotide

<400> SEQUENCE: 19
gactgcactt ctcggctcat                                               20

<210> SEQ ID NO 20
<211> LENGTH: 20
<212> TYPE: DNA
<213> ORGANISM: Artificial
<220> FEATURE:
<223> OTHER INFORMATION: Synthetic oligonucleotide
```

```
<400> SEQUENCE: 20
ccgaagctac tctccttcca                                              20

<210> SEQ ID NO 21
<211> LENGTH: 20
<212> TYPE: DNA
<213> ORGANISM: Artificial
<220> FEATURE:
<223> OTHER INFORMATION: Synthetic oligonucleotide

<400> SEQUENCE: 21
gttcagtggt gcctctgtca                                              20

<210> SEQ ID NO 22
<211> LENGTH: 20
<212> TYPE: DNA
<213> ORGANISM: Artificial
<220> FEATURE:
<223> OTHER INFORMATION: Synthetic oligonucleotide

<400> SEQUENCE: 22
actgggacga catggaaaag                                              20

<210> SEQ ID NO 23
<211> LENGTH: 20
<212> TYPE: DNA
<213> ORGANISM: Artificial
<220> FEATURE:
<223> OTHER INFORMATION: Synthetic oligonucleotide

<400> SEQUENCE: 23
cacctaccag gtgtcggaat                                              20

<210> SEQ ID NO 24
<211> LENGTH: 20
<212> TYPE: DNA
<213> ORGANISM: Artificial
<220> FEATURE:
<223> OTHER INFORMATION: Synthetic oligonucleotide

<400> SEQUENCE: 24
gtctggattg tggaggtggt                                              20

<210> SEQ ID NO 25
<211> LENGTH: 20
<212> TYPE: DNA
<213> ORGANISM: Artificial
<220> FEATURE:
<223> OTHER INFORMATION: Synthetic oligonucleotide

<400> SEQUENCE: 25
tcttctcatt cctgcttgtg                                              20

<210> SEQ ID NO 26
<211> LENGTH: 18
<212> TYPE: DNA
<213> ORGANISM: Artificial
<220> FEATURE:
<223> OTHER INFORMATION: Synthetic oligonucleotide

<400> SEQUENCE: 26
acttggtggt ttgctacg                                                18
```

MODULATION OF MRTF-A ACTIVITY IN PATHOLOGIC FIBROSIS AND WOUND HEALING

This application is a national phase application under 35 U.S.C. § 371 of International Application No. PCT/US2014/060904, filed filed Oct. 16, 2014, which claims benefit of priority to U.S. Provisional Application Ser. No. 61/891,693, filed Oct. 16, 2013, the entire contents of each of which are hereby incorporated by reference.

GOVERNMENT SUPPORT CLAUSE

This invention was made with government support under grant no. HL-077439 awarded by the National Institutes Health. The government has certain rights in the invention.

BACKGROUND OF THE INVENTION

I. Field of the Disclosure

Embodiments of this disclosure are directed generally to developmental biology, molecular genetics, and medicine. In particular, the disclosure is directed to the use of isoxazole compounds to promote wound healing.

II. Background

Fibroblasts proliferate in response to biomechanical tension or local stress signals, ultimately differentiating into smooth muscle cell (SMC)-like, contractile myofibroblasts (Eyden 2008, Hinz 2007, Hinz et al., 2001 and Tomasek et al., 2002). Myofibroblast differentiation represents a normal step in the healing process and is essential for the repair of a wide range of traumas including cutaneous injury and myocardial infarction (MI) (Tomasek et al., 2002, Tomasek et al., 2005 and Gurtner et al., 2008). Defective myofibroblast differentiation can result in abnormal or inefficient wound healing while persistent myofibroblast activation is associated with pathological fibrosis and scarring (Wynn 2008). Strategies for modulating myofibroblast number and phenotype may have therapeutic applications for the acute treatment of wounds or fibrosis-associated pathologies, however the molecular mechanisms that regulate these processes are not well understood.

The SMC phenotype is at least partially dependent upon the activity of serum response factor (SRF), which promotes cell growth or differentiation, depending upon association with distinct transcriptional coactivators (Pipes et al., 2006). Interaction with myocardin leads to the activation of genes encoding SMC contractile proteins and the differentiated phenotype (Du et al., 2003, Li et al., 2003, Small et al. 2005, Wang et al., 2001, Hoofnagle et al., 2011 and Huang et al., 2012). Mitogen-activated protein kinase (MAPK) signaling displaces myocardin from SRF by the ternary complex factor (TCF) family of Ets domain proteins, and activation of the immediate early gene response and cell proliferation (Shaw et al., 1989).

While myocardin is specifically expressed in cardiomyocytes and SMCs and is constitutively localized to the nucleus, myocardin-related transcription factor-A (MRTF-A, MKL1, MAL, BSAC) and -B (MRTF-B, MKL2) are broadly expressed and sequestered in the cytoplasm via interactions with G-actin (Pipes et al., 2006, Small et al. 2005, Wang et al., 2001, Cen et al., 2004, Wang et al., 2002 and Olson & Nordheim 2010). Situations of stress that locally alter actin dynamics and promote F-actin polymerization promote nuclear accumulation of MRTFs (Olson & Nordheim 2010, Elberg et al. 2008, Fan et al. 2007 and Zhao et a., 2007). SRF/MRTF complexes bind to consensus CArG elements (CC(A/T)6GG) within the promoters of contractile and SMC-specific target genes (Du et al., 2003, Wang et al., 2002, Olson & Nordheim 2010, Guettler et al., 2008, Miralles et al., 2003 and Kuwahara et al., 2005), most notably smooth muscle α-actin (SMA, ACTA2) and transgelin (TAGLN, SM22) (Sun et al., 2006). MRTFs are thus critical regulators of the smooth muscle contractile phenotype in response to stress.

SUMMARY OF THE INVENTION

Thus, in accordance with the present disclosure, there is provided a method of treating a wound in a subject comprising contacting the wound with a composition comprising an isoxazole or a salt or analog thereof. The wound may be a dermal wound, an epidermal wound, a burn, a laceration or abrasion, an infectious lesion, a surgical site, an ulcer (e.g., a diabetic ulcer), a puncture, a chronic wound, a scar, such as a hypertrophic scar, a keloid or a blister. The subject may be a human, a non-human mammal a reptile or a bird.

The isoxazole or a salt or analog thereof may be contacted with the wound in a wound dressing, in a gel, salve or ointment, in a topical spray, in a powder, by injection local or regional to the wound, in a topical liquid or with a suture. The method may further comprise providing to the subject a second wound therapy, such as hyperbaric oxygen therapy (HBO), negative pressure therapy (VAC), electrical stimulation, phototherapy or acoustic stimulation. The second wound therapy may alternatively be a corticosteroid, a cytotoxic drug, an antibiotic, an antiseptic, nicotine, an anti-platelet drug, an NTHE, colchicine, an anti-coagulant, a vasoconstricting drug or an immunosuppressive, a growth factor, an antibody, a protease, a protease inhibitor, an antibacterial peptide, an adhesive peptide, a hemostatic agent, living cells, honey, or nitric oxide, such as those embedded in a wound dressing.

In another embodiment, there is provided a method of inhibiting pathological dermal fibrosis and/or dermal scarring in a subject comprising contacting a tissue site with a composition comprising an inhibitor of MRTF-A. The inhibitor may be an anti-MRTF-A antibody, or a MRTF-A siRNA. The pathological dermal fibrosis may comprise keloid formation or psoriasis. The inhibitor may be delivered to said site in a wound dressing, in a gel, salve or ointment, in a topical spray, in a powder, by injection local or regional to said wound, in a topical liquid, or in a medical device.

Another embodiment comprises a device for the treatment of a wound in a subject comprising (a) a composition comprising an isoxazole or a salt or analog thereof (b) a sterile dressing into or onto which the isoxazole, salt or analog is disposed. The sterile dressing may be a compression dressing or a non-adherent dressing. The device may further comprise one or more of a lubricant, an absorber, a sponge, a wound veil, an odor control agent, and/or a cover. The isoxazole, salt or analog may be contained in a liquid, salve, ointment, gel or powder disposed in or on the sterile dressing. The sterile dressing may be a film, foam, semi-solid gel, pad, gauze, fabric. It may also be a silicone dressing, a fibrin/fibrinogen dressing, a polyacrylamide dressing, a PTFE dressing, a PGA dressing, a PLA dressing, a PLGA dressing, a polycaprolactone dressing or a hyaluronic acid dressing.

The sterile dressing may further comprise gelatin, silver, cellulose, an alginate, collagen, a hydrocolloid, a hydrogel, a skin substitute, a wound filler, a growth factor, an antibody, a protease, a protease inhibitor, an antibacterial peptide, an adhesive peptide, a hemostatic agent, living cells, honey, or nitric oxide. The sterile dressing may further comprises one or more of a corticosteroid, a cytotoxic drug, an antibiotic, an antimicrobial, an antifungal, an antiseptic, nicotine, an anti-platelet drug, an NSAID, colchicine, an anti-coagulant, a vasoconstricting drug or an immunosuppressive. The device may further comprise a substance or element for the fixation of the device to a wound, such as an adhesive or a bandage.

The device may, further comprise a port providing operable connection between the sterile dressing and a tube, including where a cover is provided for an airtight seal to or around a wound surface. The device may further comprise a drainage tube operably connected to the port at one end and suitable for attachment to a negative pressure device at another end. The sterile dressing in this embodiment may be gauze or foam.

Also provided is a method of promoting wound repair in a subject comprising contacting the wound with a device as described above. The method may further comprise applying negative pressure to the wound, may further comprise applying hyperbaric oxygen therapy to the wound, may further comprise electrical stimulation, may further comprise phototherapy, and may further comprise acoustic stimulation.

The wound may be a dermal wound, an epidermal wound, a burn, a laceration or abrasion, an infectious lesion, a surgical site, an ulcer, a puncture, a chronic wound, a scar, such as a hypertrophic scar, a keloid or a blister. The subject may be a human or a non-human mammal, a reptile, or a bird.

Also provided is a suture comprising an isoxazole or a salt or analog thereof impregnated into or disposed thereon. The suture may be an absorbable suture or a liquid suture.

Other embodiments of the disclosure are discussed throughout this application. Any embodiment discussed with respect to one aspect of the disclosure applies to other aspects of the disclosure as well and vice versa. The embodiments in the Example section are understood to be embodiments of the disclosure that are applicable to all aspects of the disclosure.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the disclosure, and vice versa. Furthermore, compositions and kits of the disclosure can be used to achieve methods of the disclosure.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any foam of containing, such as "contains" and "contain") are inclusive or open-ended and do not exclude additional, unrecited elements or method steps.

Other objects, features and advantages of the present disclosure will become apparent from the following detailed description. It should be understood, however, that the detailed description and the examples, while indicating specific embodiments of the disclosure, are given by way of illustration only, since various changes and modifications within the spirit and scope of the disclosure will become apparent to those skilled in the art from this detailed description.

DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIGS. 1C-D) Quantification of gel diameter (in FIGS. 1A and 1B) following indicated treatments. Data represents three independent experiments $*p<0.05$; $p<0.01$; $*p<0.001$; $***p<0.0001$.

(FIG. 2A) SMA immunostaining visualized by confocal microscopy at 40× magnification. Scale bar=50 µm. (FIG. 2B) qRT-PCR and (FIG. 2C) Western blot analysis of SMA and SM22 expression, as indicated, normalized to GAPDH. (FIG. 2D) Quantification of Western blot data. $*p<0.001$; $**p<0.0001$.

(FIG. 3B) To determine the effect of ISX on MRTF-dependent SMC reporter activation, cells were co-transfected with a low dose of MRTF-A (10 ng) and SMA-luc (100 ng) and then serum-starved for 24 hrs prior to treatment with 5 or 20 µM ISX. (FIG. 3C) The effect of TGF-β1 (10 ng/ml) or ISX (20 µM) treatment on basal SMA-luc activity in the absence of exogenous MRTFA. (FIG. 3D) ISX (20 µM) enhances the activation of multiple CArG-containing reporters (SMA, SM22, skeletal muscle actin (SKA), or atrial natriuretic factor (ANF)) by an intermediate dose of MRTF-A (25 ng). Mutations in the indicated CArG boxes in the ANF (FIG. 3E) or SMA (FIG. 3F) promoters ablate responsiveness to ISX. Data is normalized to βgal internal control and expressed relative to empty vector (A, B, D, E, F) or vehicle (C). $*p<0.05$; $p<0.01$; $*p<0.001$; $****p<0.0001$.

FIGS. 4A-E. ISX induces endogenous MRTF targets. BR5 dermal fibroblasts infected with 10 MOI adenovirus expressing flag-MRTF-A, were serum-starved and then treated with ISX (20 µM), TGF-β1 or vehicle for 48 hrs, as indicated. (FIG. 4A) SMA positive stress fibers were visualized by confocal microscopy at 40× magnification. Scale bar=50 μm. (FIG. 4B) Expression of SMA and SM22 was analyzed by qRT-PCR. Data is normalized to GAPDH. (FIG. 4C) Levels of SMA protein were analyzed by Western blot. (FIG. 4D) Levels of MRTF-A and SMA were examined by Western blot in MRTF-A wild-type (WT) and KO tail tip dermal fibroblasts treated with vehicle or ISX. (FIG. 4E) Quantification of SMA protein levels normalized to GAPDH. *p<0.05. p<0.01; **p<0.0001.

FIGS. 5A-E. ISX promotes MRTF-A enrichment and nuclear accumulation. NIH/3T3 fibroblasts infected with 25 MOI adenovirus expressing HA-tagged MRTF-A and treated with ISX (20 μM) or vehicle. (FIG. 5A) ISX promotes the enrichment and nuclear accumulation of MRTF-A (green) as visualized by HA immunostaining and confocal microscopy at 60× magnification. SMA (red) is enriched in stress fibers of MRTF-A expressing cells. Scale bar=50 μm. (FIG. 5B) Quantification of cells with HA-MRTF-A in nucleus only, cytoplasm only or in both. Data represent three independent experiments. (FIG. 5C) Forced expression of flag-MRTF-A (10MOI) demonstrates enrichment in ISX treated cells. (FIG. 5D) SRF protein levels are enriched with ISX treatment, while panfibroblast markers (Fsp1 and vimentin) are not. (FIG. 5E) ISX treatment leads to phosphorylation of Erk1/2, but not Smad2/3, as demonstrated by Western blot. ****p<0.0001.

(FIG. 6A) Expression of MRTF-A and myofibroblast markers was analyzed 7 days post-injury by qRT-PCR. Data is normalized to GAPDH. (FIG. 6B) H&E (a, d) andMasson's trichrome staining (b, c, e, f) of ISX- or vehicle-treated wounds (7 days post-injury) depicting the migrating epidermal sheets (black arrow) and granulation tissue area, 4× (a, b, d, e) and 40× (c, f) magnification. Scale bar=500 μm (4×) or 50 μm (40×). (FIG. 6C) Quantification of distance between epithelial sheets or granulation tissue layers in the healing wound. n=4-8 (FIG. 6D) Immunofluorescent detection of SMA in ISX or vehicle-treated cutaneous wounds. Dashed line denotes border of wound and boxed area identifies area of granulation tissue shown in (b, d). Scale bar=200 μm (a, c) and 50 μm (b, d) (FIG. 6E) Quantification of the depth of SMA positive granulation tissue. E-epidermis; D-dermis; GT-granulation tissue. *p<0.05; **p<0.01.

(FIG. 13A) Wild-type or MRTF-A KO mice were subjected to full-thickness cutaneous wounds and imaged over the course of 11 d. (FIG. 13B) Quantification of the wound areas using National Institutes of Health ImageJ (n=10). (FIG. 13C) H&E (a, d) and Masson's trichrome staining (b, c, e, f) of WT or MRTF-A KO wounds depicting the migrating epidermal sheets (black arrow) and granulation tissue area [4× (a, b, d, e) and 40× (c, f) magnification]. [Scale bar, 500 μm (4×) or 50 μm (40×).]

DETAILED DESCRIPTION OF THE INVENTION

Figures 1A, 1B:
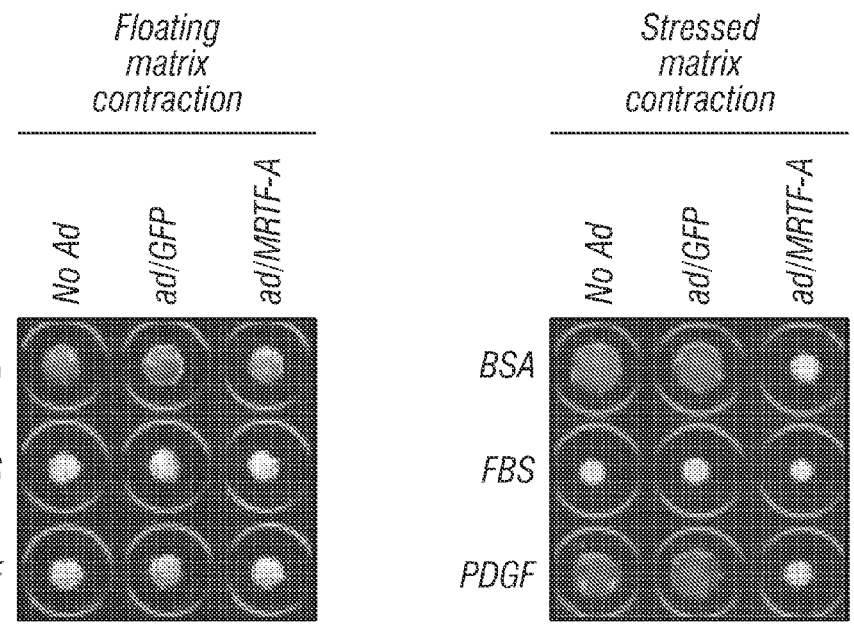
FIGS. 1A-D. MRTF-A promotes fibroblast contractility. BR5 human dermal fibroblasts were infected with 25 MOI adenovirus expressing flag-MRTFA or GFP control and cultured in a collagen matrix overnight. Floating (FIG. 1A) or stressed (FIG. 1B) collagen gels were imaged after stimulation with growth factor (FBS or PDGF) or BSA control for 1 hour.

Previously, the inventors found that MRTF-A promotes differentiation of cardiac fibroblasts to a myofibroblast phenotype and production of stress fibers (Small et al., 2010). Deletion of MRTF-A in mice attenuates myofibroblast responses following cardiac injury and reduces cardiac fibrosis and scarring (Small et al., 2010). In this study, the inventors demonstrate that MRTF-A stimulates fibroblast contractility, while MRTF-A null fibroblasts fail to induce the SMC contractile program in response to stress signals. An isoxazole (ISX) ring-containing small molecule previously shown to induce SMA expression in cardiac progenitor cells (Russell et al., 2012) activates fibroblast differentiation via the induction of MRTF-A activity. These findings implicate the MRTF-SRF gene regulatory axis as a key mediator of myofibroblast differentiation and wound healing, and suggest that therapeutic manipulation of this pathway may provide benefit in diseases associated with inappropriate myofibroblast differentiation. These and other aspects of the disclosure are discussed further below.

I. MYOCARDIN-RELATED TRANSCRIPTION FACTOR A

Serum response factor (SRF) plays a primary role in the regulation of nearly every known smooth muscle-specific gene via binding to the sequence [CC(A/T)$_6$GG], termed a CArG box or serum response element (SRE) (Pipes et al., 2006; Miano, 2003). The transcriptional activity of SRF is enhanced through its association with the coactivators myocardin and the myocardin-related transcription factors (MRTF-A/MAL/MKLJ and MRTF-B/MKL2) (Pipes et al., 2006; Wang et al., 2001; Wang et al., 2002; Can et al., 2004).

Myocardin is restricted to cardiac and smooth muscle and is required and sufficient with SRF for the activation of smooth muscle gene expression (Wang et al., 2001; Wang et al., 2003; Small et al., 2005; Li et al., 2003; Du et al., 2003). MRTF-A and MRTF-B are broadly expressed and are regulated at the level of subcellular distribution via interactions with the actin cytoskeleton (Wang et al., 2002; Miralles et al., 2003; Oh et al., 2005; Li et al., 2006). MRTF-A and MRTF-B possess a unique N-terminal RPEL domain that mediates binding to G-actin and cytoplasmic sequestration (Guettler et al., 2008).

Stress signals, mechanical force, and changes in cell shape result in the activation of Rho-Rho-kinase (ROCK) signaling, reorganization of the actin cytoskeleton, and nuclear translocation of MRTF-A, thereby linking actin dynamics to SRF-dependent gene transcription (Miralles et al., 2003; Kuwahara et al., 2005; Kuwahara et al., 2007; Zhao et al., 2007; Mack et al., 2001; Philippar et al., 2004; Olson and Nordheim, 2010). ROCK-dependent signaling enhances the transcription of genes encoding ECM components and SMA by myofibroblastlike cells in models of fibrotic pathology (Akhmetshina et al., 2008; Fan et al., 2007; Fu et al., 2006; Fukushima et al., 2005).

ROCK haploinsufficiency or pharmacological inhibition of ROCK reduces cardiac fibrosis in response to MI, ischemic reperfusion, or pressure overload (Rikitake et al., 2005; Hamid et al., 2007; Hattori et al., 2004; Zhang et al., 2006; Haudek et al., 2009) ROCK activation contributes to the nuclear accumulation of MRTFs and the activation of SMA transcription in vitro (Fan et al., 2007; Elberg et al., 2008). An SRF-containing complex has been implicated in the induction of a myofibroblast phenotype (Qiu et al., 2003; Qiu et al., 2005), but whether SRF contributes to fibrosis in vivo is unknown.

II. MODULATION OF MRTF-A

A. Isoxazole Compounds as Therapeutic Agents

Compounds of the present disclosure may be considered as derived from isoxazoles. The following compounds are representative of certain compounds of the present disclosure:

a compound of formula (I):

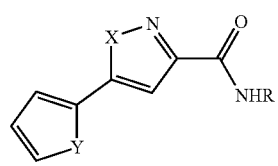

wherein X is O or NH, Y is S or O and R is H, a substituted or unsubstituted alkyl, such as $C_1$-$C_6$ alkyl or $C_3$-$C_6$ cycloalkyl, or a substituted or unsubstituted alkenyl, such as $C_2$-$C_6$ alkenyl, a substituted or unsubstituted alkynyl, such as $C_2$-$C_6$ alkynyl, or a stereoisomer, solvate, hydrate, or pharmaceutically acceptable salt thereof. In certain embodiments regarding compounds of formula (I), the proviso exists such that with the provisos that if X is O, then R must be a substituted or unsubstituted $C_3$-$C_6$ cycloalkyl; and/or if X is NH, then R must not be pyrazinyl substituted $C_1$-$C_6$ alkyl;

a compound of formula (Ia), (Ib), or (Ic):

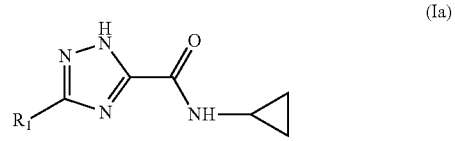

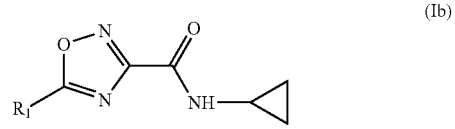

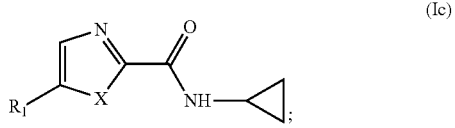

wherein $R_1$ is substituted or unsubstituted phenyl, unsubstituted pyrrolyl, unsubstituted pyridyl, unsubstituted furanyl, unsubstituted thienyl, unsubstituted benzofuranyl, unsubstituted benzo[b]thiophenyl, or unsubstituted thiazolyl. Any of these R1 substituents may be substituted as well;

a compound of formula (II):

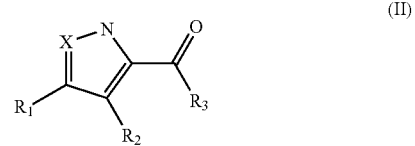

wherein: $R_1$ is substituted or unsubstituted phenyl, substituted or unsubstituted thiophenyl or a substituent of formula (A):

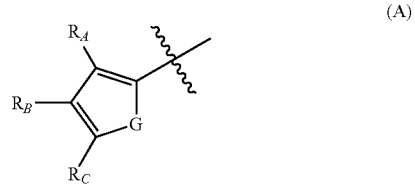

wherein: $R_A$, $R_B$ and $R_C$ are each independently selected from the group consisting of hydrogen, halogen, $C_1$-$C_6$ alkyl, $C_3$-$C_6$ cycloalkyl, aryl, cyano, nitro, and a carbonyl group; and G is O, —NH, or S; $R_2$ is hydrogen, hydroxy, halogen, nitro, aryl, alkyl, alkoxy, alkenyl, alkenyloxy, alkynyl, alkynyloxy, aralkyl, —CHO, —C(O)$R_9$, —OC(O)$R_9$, —OC(O)O$R_9$, —O(CN)O$R_9$, —C(O)N$R_9R_{10}$, —OC(O) N$R_9R_{10}$, —N$R_9R_5$, or —SO$_3R_9$; wherein $R_9$ and $R_{10}$ are each independently hydrogen, alkyl, aryl, or aralkyl; $R_3$ is —NH—O-alkyl, —NH—OH, —O$R_{11}$ or —N$R_{11}R_{12}$, wherein $R_{11}$ and $R_{12}$ are each independently hydrogen, alkyl, alkenyl, alkynyl, aryl, or aralkyl; or $R_{11}$ and $R_{12}$ together form a cyclic group; or $R_{11}$ and $R_{12}$ together with the nitrogen to which they are bound form a cyclic group; X is O or —N$R_{13}$, wherein $R_{13}$ is hydrogen, alkyl, aryl, or aralkyl; or a stereoisomer, solvate, hydrate, or pharmaceutically acceptable salt thereof;

and a compound having formula (V):

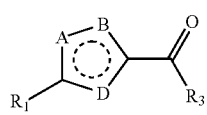

wherein: the ABD ring comprises two non-adjacent double bonds; A, B and D are each independently S, N, O, C, —NR$_{14}$, —CR$_{15}$, or —CR$_{15}$R$_{16}$, wherein R$_{14}$ is hydrogen, halogen, alkyl, aryl, or aralkyl; and R$_{15}$ and R$_{16}$ are each independently hydrogen, hydroxy, halogen, nitro, aryl, alkyl, alkoxy, alkenyl, alkenyloxy, alkynyl, alkynyloxy, aralkyl, —CHO, —C(O)R$_9$, —OC(O)R$_9$, —OC(O)OR$_9$, —O(CN)OR$_9$, —C(O)NR$_9$R$_{10}$, —OC(O)NR$_9$R$_{10}$, —NR$_9$OR$_5$, or —SO$_3$R$_9$; wherein R$_9$ and R$_{10}$ are each independently hydrogen, alkyl, aryl, or aralkyl, provided that at least two of A, B and D comprise S, N, or O; R$_1$ is alkyl, —CH=CH-aryl, or aryl; and R$_3$ is alkyl, aryl, aralkyl, —OR$_4$, or —NR$_4$R$_5$, wherein: R$_4$ and R$_5$ are each independently hydrogen, alkyl, aryl, or aralkyl; or R$_4$ and R$_5$ together form a cyclic group; or R$_4$ and R$_5$ together with the nitrogen to which they are bound form a cyclic group. In certain embodiments regarding compounds of formula (V), the proviso exists such that compounds of formula (V$_a$) are excluded:

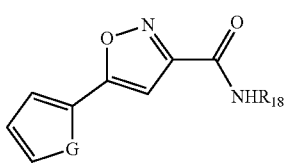

wherein R$_{18}$ is alkyl, such as lower alkyl or cyclopentyl, or alkenyl, such as lower alkenyl or allyl, and G is O or S.

B. Chemical Definitions

When used in the context of a chemical group, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylimino); "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S In the context of chemical formulas, the symbol "—" means a single bond, "=" means a double bond, and "≡" means triple bond. The symbol "- - - -" represents an optional bond, which if present is either single or double. The symbol "═══" represents a single bond or a double bond. Thus, for example, the structure

includes the structures

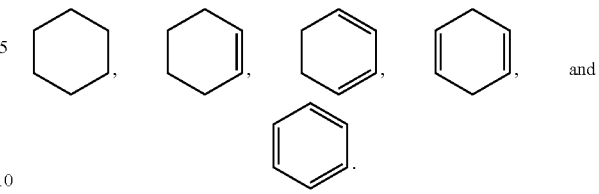

As will be understood by a person of skill in the art, no one such ring atom forms part of more than one double bond. The symbol "⁓", when drawn perpendicularly across a bond indicates a point of attachment of the group. It is noted that the point of attachment is typically only identified in this manner for larger groups in order to assist the reader in rapidly and unambiguously identifying a point of attachment. The symbol "◢" means a single bond where the group attached to the thick end of the wedge is "out of the page." The symbol "⫶⫶⫶" means a single bond where the group attached to the thick end of the wedge is "into the page". The symbol "⁓" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

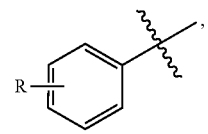

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

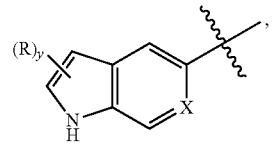

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C\leq 8)}$" or the class "alkene$_{(C\leq 8)}$" is two. For example, "alkoxy$_{(C\leq 10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neopentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CHF, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. The term "alkynediyl" when used without the "substituted" modifier refers to a divalent unsaturated aliphatic group, with two carbon atoms as points of attachment, a linear or branched, cyclo, cyclic or acyclic structure, at least one carbon-carbon triple bond, and no atoms other than carbon and hydrogen. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

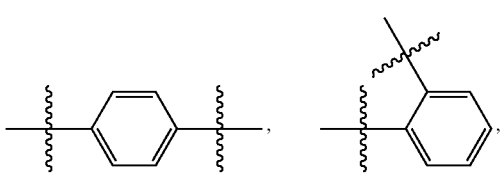

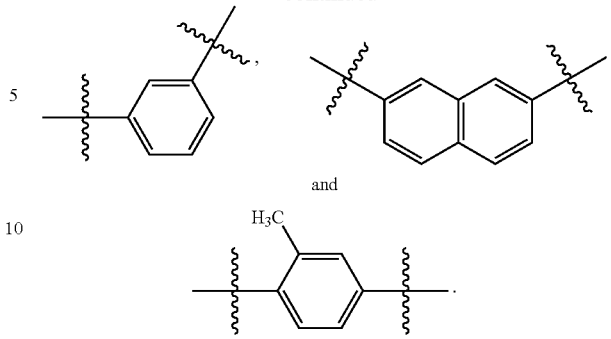

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the group consists of no atoms other than carbon, hydrogen, aromatic nitrogen, aromatic oxygen and aromatic sulfur. As used herein, the term does not preclude the presence of one or more alkyl group (carbon number limitation permitting) attached to the aromatic ring or any additional aromatic ring present. Non-limiting examples of heteroaryl groups include furanyl, imidazolyl, indolyl, indazolyl (Im), methylpyridyl, oxazolyl, pyridyl, pyrrolyl, pyrimidyl, pyrazinyl, quinolyl, quinazolyl, quinoxalinyl, thienyl, and triazinyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of heteroarenediyl groups include:

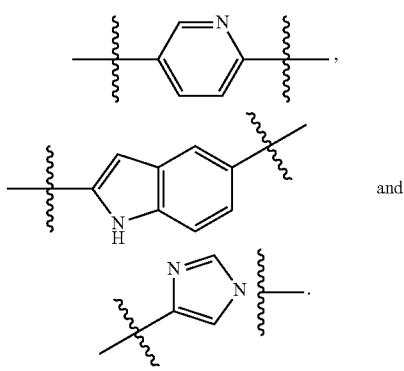

and

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, C(O)CH$_2$CH$_2$CH$_3$, C(O)CH(CH$_3$)$_2$, C(O)CH(CH$_2$)$_2$, C(O)C$_6$H$_5$, C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. Similarly, the term "alkylthio" when used without the "substituted" modifier refers to the group —SR, in which R is an alkyl, as that term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

Modifications or derivatives of the compounds, agents, and active ingredients disclosed throughout this specification are contemplated as being useful with the methods and compositions of the present disclosure. Derivatives may be prepared and the properties of such derivatives may be assayed for their desired properties by any method known to those of skill in the art.

In certain aspects, "derivative" refers to a chemically modified compound that still retains the desired effects of the compound prior to the chemical modification. "Isoxazole derivatives," therefore, refers to a chemically modified compound that still retains the desired effects of the parent isoxazole prior to its chemical modification. Such effects may be enhanced (e.g., slightly more effective, twice as effective, etc.) or diminished (e.g., slightly less effective, 2-fold less effective, etc.) relative to the parent isoxazole, but may still be considered an isoxazole derivative. Such derivatives may have the addition, removal, or substitution of one or more chemical moieties on the parent molecule. Non-limiting examples of the types modifications that can be made to the compounds and structures disclosed herein include the addition or removal of lower unsubstituted alkyls such as methyl, ethyl, propyl, or substituted lower alkyls such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

Prodrugs and solvates of the compounds of the present disclosure are also contemplated herein. The term "prodrug" as used herein, is understood as being a compound which, upon administration to a subject, such as a mammal, undergoes chemical conversion by metabolic or chemical processes to yield a compound any of the formulas herein, or a salt and/or solvate thereof (Bundgaard, 1991; Bundgaard, 1985). Solvates of the compounds of the present disclosure are preferably hydrates.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the agents of the disclosure with an organic base such as methylamine, ethylamine, ethanolamine, lysine, ornithine and the like.

Pharmaceutically acceptable salts include the salts formed between carboxylate or sulfonate groups found on some of the compounds of this disclosure and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, Selection and Use* (2002), which is incorporated herein by reference.

As used herein, the term "cyclic group" refers to a carbocycle group (e.g., cyclopropyl, cyclohexyl), a heterocycle group (e.g., pyrrolidinyl), an aryl group, or any combination thereof (e.g., fused bicyclic group).

As used herein, "protecting group" refers to a moiety attached to a functional group to prevent an otherwise unwanted reaction of that functional group. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups may be found in Greene and Wuts (1999). Compounds of the present disclosure are specifically contemplated wherein one or more functional groups are protected by a protecting group.

Compounds of the present disclosure may contain one or more asymmetric centers and thus can occur as racemates and racemic mixtures, single enantiomers, diastereomeric mixtures and individual diastereomers. In certain embodiments, a single diastereomer is present. All possible stereoisomers of the compounds of the present disclosure are contemplated as being within the scope of the present disclosure. However, in certain aspects, particular diastereomers are contemplated. The chiral centers of the compounds of the present disclosure can have the S- or the R-configuration, as defined by the IUPAC 1974 Recommendations. In certain aspects, certain compounds of the present disclosure may comprise S- or R-configurations at particular carbon centers. For example, the following specific compounds contain asymmetric centers:

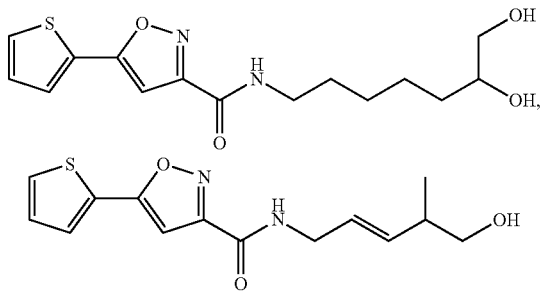

and are thus claimed as a racemic mixture (+/−), R (+) and S (−) forms.

Solvent choices for the synthetic preparation of compounds of the present disclosure will be known to one of ordinary skill in the art. Solvent choices may depend, for example, on which one(s) will facilitate the solubilizing of all the reagents or, for example, which one(s) will best facilitate the desired reaction (particularly when the mechanism of the reaction is known). Solvents may include, for example, polar solvents and non-polar solvents. Solvents choices include, but are not limited to, tetrahydrofuran, dimethylformamide, dimethylsulfoxide, dioxane, methanol, ethanol, hexane, methylene chloride and acetonitrile. More than one solvent may be chosen for any particular reaction or purification procedure. Water may also be admixed into any solvent choice. Further, water, such as distilled water, may constitute the reaction medium instead of a solvent.

Persons of ordinary skill in the art will be familiar with methods of purifying compounds of the present disclosure. One of ordinary skill in the art will understand that compounds of the present disclosure can generally be purified at any step, including the purification of intermediates as well as purification of the final products. In particular embodiments, purification is performed via silica gel column chromatography or HPLC.

In view of the above definitions, other chemical terms used throughout this application can be easily understood by those of skill in the art. Terms may be used alone or in any combination thereof. The preferred and more preferred chain lengths of the radicals apply to all such combination.

C. Inhibitors of MRTF-A

The present disclosure contemplates the use of virtually any composition that will inhibit MRTF-A function. Organopharmaceutical compounds that produce the desired effect would find great utility, and such compounds may be identified according to the screening methods described above. In addition, biological inhibitors, as described below, may be utilized to interfere with MRTF-A expression or function.

1. Antisense Constructs

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

2. Ribozymes

Another general class of inhibitors is ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). It has also been shown that ribozymes can elicit genetic changes in some cells lines to which they were applied; the altered genes included the oncogenes H-ras, c-fos and genes of HIV. Most of this work involved the modification of a target mRNA, based on a specific mutant codon that was cleaved by a specific ribozyme.

3. RNAi RNA interference (also referred to as "RNA-mediated interference" or RNAi) is another mechanism by which protein expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin et al., 1999; Montgomery et al., 1998; Sharp et al., 2000; Tabara et al., 1999). Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene (Fire et al., 1998; Grishok et al., 2000; Ketting et al., 1999; Lin et al., 1999; Montgomery et al., 1998; Sharp, 1999; Sharp et al., 2000; Tabara et al., 1999). Moreover, dsRNA has been shown to silence genes in a wide range of systems, including plants, protozoans, fungi, *C. elegans, Trypanasoma, Drosophila*, and mammals (Grishok et al, 2000; Sharp, 1999; Sharp et al., 2000; Elbashir et al., 2001). It is generally accepted that RNAi acts post-transcriptionally, targeting RNA transcripts for degradation, and possibly by inhibiting translation. It appears that both nuclear and cytoplasmic RNA can be targeted (Bosher et al., 2000).

siRNAs must be designed so that they are specific and effective in suppressing the expression of the genes of interest. Methods of selecting the target sequences, i.e. those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998). Of particular interest are those siRNAs that span an exon-intron junction.

The making of siRNAs has been mainly through direct chemical synthesis; through processing of longer, double stranded RNAs through exposure to *Drosophila* embryo lysates; or through an in vitro system derived from S2 cells. Use of cell lysates or in vitro processing may further involve the subsequent isolation of the short, 21-23 nucleotide siRNAs from the lysate, etc., making the process somewhat cumbersome and expensive. Chemical synthesis proceeds by making two single stranded RNA-oligomers followed by the annealing of the two single stranded oligomers into a double stranded RNA. Methods of chemical synthesis are diverse. Non-limiting examples are provided in U.S. Pat. Nos. 5,889,136, 4,415,732, and 4,458,066, expressly incorporated herein by reference, and in Wincott et al. (1995).

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy)thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

Chemically synthesized siRNAs are found to work optimally when they are in cell culture at concentrations of 25-100 nM. This had been demonstrated by Elbashir et al. (2001) wherein concentrations of about 100 nM achieved effective suppression of expression in mammalian cells. siRNAs have been most effective in mammalian cell culture at about 100 nM. In several instances, however, lower concentrations of chemically synthesized siRNA have been used (Caplen et al., 2000; Elbashir et al., 2001).

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. See U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25 mer lengths with the endogenous nuclease complex that converts long dsRNAs to siRNAs in vivo. They do not describe or present data for synthesizing and using in vitro transcribed 21-25 mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single stranded RNA is enzymatically synthesized from the PCR™ products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates can be attached to a solid surface. After transcription with RNA polymerase, the resulting dsRNA fragments may be used for detecting and/or assaying nucleic acid target sequences.

In a specific embodiment, the inventors propose to inhibit MRTF-A expression in adult tissues in vitro using siRNA or shRNA in an adenoviral vector. A GFP marker can be utilized to determine cells that take up the vector, and thus permit checking for appropriate inhibition of MRTF-A production. The use of an inducible promoter that allows for induction of the siRNA or shRNA only under specific growth conditions permit reversible inhibition of MRTF-A.

4. Antibodies

In certain aspects of the disclosure, antibodies may find use as inhibitors of MRTF-A. As used herein, the term "antibody" is intended to refer broadly to any appropriate immunologic binding agent such as IgG, IgM, IgA, IgD and IgE. Generally, IgG and/or IgM are preferred because they are the most common antibodies in the physiological situation and because they are most easily made in a laboratory setting.

The term "antibody" also refers to any antibody-like molecule that has an antigen binding region, and includes antibody fragments such as Fab', Fab, F(ab').sub.2, single domain antibodies (DABs), Fv, scFv (single chain Fv), and the like. The techniques for preparing and using various antibody-based constructs and fragments are well known in the art.

Monoclonal antibodies (MAbs) are recognized to have certain advantages, e.g., reproducibility and large-scale production, and their use is generally preferred. The disclosure thus provides monoclonal antibodies of the human, murine, monkey, rat, hamster, rabbit and even chicken origin. Due to the ease of preparation and ready availability of reagents, murine monoclonal antibodies will often be preferred. Single-chain Mabs are described in U.S. Pat. Nos. 4,946,778 and 5,888,773, each of which are hereby incorporated by reference. The present disclosure would most likely utilize single-chain antibodies expressed from expression vectors, as described below.

"Humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's dental disease are likewise known and such custom-tailored antibodies are also contemplated.

Of particular interest here are intrabodies, which are antibodies that work within the cell to bind to an intracellular protein. Due to the lack of a reliable mechanism for bringing antibodies into the cell from the extracellular environment, this typically requires the expression of the antibody within the target cell, which can be accomplished by gene therapy. As a result, intrabodies are defined as antibodies that have been modified for intracellular localization This term can apply to several types of protein targeting: the antibody may remain in the cytoplasm, or it may have a nuclear localization signal, or it may undergo cotranslational translocation across the membrane into the lumen of the endoplasmic reticulum, provided that it is retained in that compartment through a KDEL sequence.

III. METHODS OF TREATING WOUNDS

Wound healing, or wound repair, is an intricate process in which the skin (or another organ-tissue) repairs itself after injury. In normal skin, the epidermis (outermost layer) and dermis (inner or deeper layer) exists in a steady-state equilibrium, forming a protective barrier against the external environment. Once the protective barrier is broken, the normal (physiologic) process of wound healing is immediately set in motion. The classic model of wound healing is divided into three or four sequential yet overlapping phases: (1) hemostasis, (2) inflammatory, (3) proliferative and (4) remodeling. Upon injury to the skin, a set of complex biochemical events takes place in a closely orchestrated cascade to repair the damage. Within minutes post-injury, platelets (thrombocytes) aggregate at the injury site to form a fibrin clot. This clot acts to control active bleeding (hemostasis).

In the inflammatory phase, bacteria and debris are phagocytosed and removed, and factors are released that cause the migration and division of cells involved in the proliferative phase.

The proliferative phase is characterized by angiogenesis, collagen deposition, granulation tissue formation, epithelialization, and wound contraction. In angiogenesis, new blood vessels are formed by vascular endothelial cells. In fibroplasia and granulation tissue formation, fibroblasts grow and form a new, provisional extracellular matrix (ECM) by excreting collagen and fibronectin. Concurrently, re-epithelialization of the epidermis occurs, in which epithelial cells proliferate and 'crawl' atop the wound bed, providing cover for the new tissue.

In contraction, the wound is made smaller by the action of myofibroblasts, which establish a grip on the wound edges and contract themselves using a mechanism similar to that in smooth muscle cells. When the cells' roles are close to complete, unneeded cells undergo apoptosis.

In the maturation and remodeling phase, collagen is remodeled and realigned along tension lines and cells that are no longer needed are removed by apoptosis. However, this process is not only complex but fragile, and susceptible to interruption or failure leading to the formation of chronic non-healing wounds. Factors which may contribute to this include diabetes, venous or arterial disease, old age, and infection. The phases of wound healing normally progress in a predictable, timely manner; if they do not, healing may progress inappropriately to either a chronic wound such as a venous ulcer or pathological scarring such as a keloid scar.

Treatment of wounds depends on how severe the wound is, its location, and whether other areas are affected. If another condition is causing problems with wound healing, it is important to treat or control this problem. A caregiver may prescribe antibiotics to fight infection, either orally, i.v., or applied directly on the wound area. Palliative care such as for pain, swelling and fever are often prescribed. Wound care is essential as well and includes cleansing, debridement and wound dressing. Dressings are particularly important to protect the wound from further injury and infection. These may also help give pressure to decrease swelling. Dressings may be in the form of bandages, films, or foams. They may contain certain substances that may help promote faster healing. Sometimes, skin taken from another part of the body may be used to close a large wound. The skin may also be man-made, which contains special cells needed to repair damaged tissues. Additional treatments include hyperbaric oxygen therapy (HBO), negative pressure therapy (also called vacuum-assisted closure or "VAC"), or creams, ointments, or medicines with special solutions which help in wound healing may be applied to the wound.

IV. COMBINED THERAPIES

In the context of the present disclosure, it is contemplated that the isoxazoles, or salts or analogs thereof may be used in combination with a second therapeutic agent to more effectively treat wounds. Additional therapeutic agents contemplated for use in combination with the isoxazole compound, or salts or analogs thereof include, but are not limited to other wound healing agents, protective agents, and scar reducing agents and the like. Specific examples include corticosteroids, cytotoxic drugs, antibiotics, antiseptics, nicotine, anti-platelet drugs, NSAIDS, colchicines, anticoagulants, vasoconstricting drugs and immunosuppressives, as well as HBO and VAC methods, discussed above.

To aid in the wound healing process, using the methods and compositions of the present disclosure, one would generally contact a cell with a isoxazole compound, or salts or analogs thereof in combination with a second agent. These compositions would be provided in a combined amount effective to exert a combined effect on the damaged tissue. This process may involve contacting the cells with isoxazole, or salts or analogs thereof in combination with a second therapeutic agent or factor(s) at the same time. This may be achieved by contacting the cell with a single composition or pharmacological formulation that includes both agents, or by contacting the cell with two distinct compositions or formulations, at the same time, wherein one composition includes the isoxazole or derivatives thereof and the other includes the second agent.

Alternatively, treatment with isoxazole, or salts or analogs thereof may precede or follow the additional agent treatment by intervals ranging from minutes to weeks. In embodiments where the second agent is applied separately to the target, one would generally ensure that a significant period of time did not expire between the time of each delivery, such that the agent would still be able to exert an advantageously combined effect on the target. In such instances, it is contemplated that one would contact the target with both modalities within about 12-24 hr of each other and, more preferably, within about 6-12 hr of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either isoxazole or salts, or analogs thereof in combination with a second therapeutic agent will be desired. Various combinations may be employed, where isoxazole or salts or analogs thereof is "A" and the second therapeutic agent is "B", as exemplified below:

| A/B/A | B/A/B | B/B/A | A/A/B | B/A/A | A/B/B |
|-------|-------|-------|-------|-------|-------|
| B/B/B/A | B/B/A/B | A/A/B/B | A/B/A/B | A/B/B/A | B/B/A/A |

-continued

| B/A/B/A | B/A/A/B | B/B/B/A | A/A/A/B | B/A/A/A | A/B/A/A |
|---------|---------|---------|---------|---------|---------|
| A/A/B/A | A/B/B/B | B/A/B/B | B/B/A/B | | |

Other combinations are contemplated.

In the present disclosure, a number of drugs or agents may prove particularly useful when combined with an isoxazole or salts or analogs thereof. Such agents/drugs include corticosteroids, NSAIDs or any other anti-inflammatory, a cytotoxic drug, an antibiotic, antimicrobial, antifungal or antiseptic, nicotine, an anti-platelet drug, colchicine, anticoagulants, vasoconstricting drugs or immunosuppressives.

V. FORMULATIONS AND ROUTES FOR ADMINISTRATION

Where clinical applications are contemplated, it will be necessary to prepare pharmaceutical compositions of isoxazole or salts or analogs thereof, or any additional therapeutic agent disclosed herein in a form appropriate for the intended application. Generally, this will entail preparing compositions that are essentially free of pyrogens, as well as other impurities that could be harmful to humans or animals.

One will generally desire to employ appropriate salts and buffers to allow for proper administration. Aqueous compositions of the present disclosure in an effective amount may be dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the agents of the present disclosure, its use in therapeutic compositions is contemplated. Supplementary active ingredients also can be incorporated into the compositions.

The composition(s) of the present disclosure may be delivered orally, nasally, intramuscularly, or intraperitoneally, but in particular the disclosure is designed for topical or mucosal application. In some embodiments, local or regional delivery of isoxazole or salts or analogs thereof alone, or in combination with a second therapeutic agent, to a wound are contemplated. Other examples of delivery of the compounds of the present disclosure that may be employed include intra-arterial, intracavity, intravesical, intrathecal, intrapleural, and intraperitoneal routes. Systemic delivery may be appropriate in certain circumstances.

The active compositions of the present disclosure may include classic pharmaceutical preparations. Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms. The therapeutic compositions of the present disclosure may be administered in the form of injectable compositions either as liquid solutions or suspensions; solid forms suitable for solution in, or suspension in, liquid prior to injection may also be prepared. These preparations also may be emulsified.

A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH, exact concentration of the various components, and the pharmaceutical composition are adjusted according to well known parameters. Suitable excipients for formulation with isoxazole or salts or analogs thereof include croscarmellose sodium, hydroxypropyl methylcellulose, iron oxides synthetic), magnesium stearate, microcrystalline cellulose, polyethylene glycol 400, polysorbate 80, povidone, silicon dioxide, titanium dioxide, and water (purified).

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent(s) of the present disclosure is determined based on the intended goal, for example (i) inhibition of tumor cell proliferation or (ii) elimination of tumor cells. The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

VI. THERAPEUTICALLY EFFECTIVE AMOUNTS OF THERAPEUTIC COMPOSITIONS

A therapeutically effective amount of isoxazole, or salts, or analogs thereof alone, or in combination with a second therapeutic agent such as an anticancer agent as a treatment varies depending upon the host treated and the particular mode of administration. In one embodiment of the disclosure the dose range of the isoxazoles or salts or analogs thereof alone, or in combination with a second agent used will be about 0.5 mg/kg body weight to about 500 mg/kg body weight. The term "body weight" is applicable when an animal is being treated. When isolated cells are being treated, "body weight" as used herein should read to mean "total cell weight". The term "total weight may be used to apply to both isolated cell and animal treatment. All concentrations and treatment levels are expressed as "body weight" or simply "kg" in this application are also considered to cover the analogous "total cell weight" and "total weight" concentrations. However, those of skill will recognize the utility of a variety of dosage range, for example, 1 mg/kg body weight to 450 mg/kg body weight, 2 mg/kg body weight to 400 mg/kg body weight, 3 mg/kg body weight to 350 mg/kg body weight, 4 mg/kg body weight to 300 mg/kg body weight, 5 mg/kg body weight to 250 mg/kg body weight, 6 mg/kg body weight to 200 mg/kg body weight, 7 mg/kg body weight to 150 mg/kg body weight, 8 mg/kg body weight to 100 mg/kg body weight, or 9 mg/kg body weight to 50 mg/kg body weight. Further, those of skill will recognize that a variety of different dosage levels will be of use, for example, 1 mg/kg, 2 mg/kg, 3 mg/kg, 4 mg/kg, 5 mg/kg, 7.5 mg/kg, 10 mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1500 mg/kg, 1750 mg/kg, 2000 mg/kg, 2500 mg/kg, and/or 3000 mg/kg. Of course, all of these dosages are exemplary, and any dosage in-between these points is also expected to be of use in the disclosure. Any of the above dosage ranges or dosage levels may be employed for isoxazole, or salts or analogs thereof in combination with a second therapeutic agent.

"Therapeutically effective amounts" are those amounts effective to produce beneficial results, particularly with respect to wound healing, in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As is well known in the art, a specific dose level of active compounds such as isoxazole or salts or analogs thereof alone, or in combination with a second therapeutic agent, for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

In some embodiments, isoxazole or salts or analogs thereof alone, or in combination with a second therapeutic agent will be administered. When a second therapeutic agent is administered, as long as the dose of the second therapeutic agent does not exceed previously quoted toxicity levels, the effective amounts of the second therapeutic agents may simply be defined as those amounts effective to reduce the cancer growth when administered to an animal in combination with the isoxazole or salts or analogs thereof. This may be easily determined by monitoring the animal or patient and measuring those physical and biochemical parameters of health and disease that are indicative of the success of a given treatment. Such methods are routine in animal testing and clinical practice.

In some embodiments of the present disclosure may be administered, as is typical, in regular cycles. A cycle may involve one dose, after which several days or weeks without treatment ensues for normal tissues to recover from possible side effects. Doses may be given several days in a row, or every other day for several days, followed by a period of rest. One would generally ensure that a significant period of time did not expire between the time of each delivery, such that the agent would still be able to exert an continuous effect on the target. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. If more than one drug is used, the treatment plan will specify how often and exactly when each drug should be given. The number of cycles a person receives may be determined before treatment starts (based on the type, location and severity of the wound) or may be flexible, in order to take into account how quickly the wound is healing. Certain serious side effects may also require doctors to adjust the therapy to allow the patient time to recover.

VII. DEVICES FOR DELIVERY OF THERAPEUTIC COMPOUNDS

The present disclosure involves, in some aspects, the provision of devices for delivery of isoxazole compounds to wounds. In general, it is contemplated that any device or material that is brought into contact with a wound is a suitable vehicle for delivering isoxazole compounds. The following devices/materials are exemplary in nature and are not meant to be limiting.

A. Wound Dressings

The present disclosure, in one aspect, provides for various wound dressings that incorporate or have applied thereto the isoxazole compounds of the present disclosure. Dressings have a number of purposes, depending on the type, severity and position of the wound, although all purposes are focused towards promoting recovery and preventing further harm from the wound. Key purposes of are dressing are to seal the wound and expedite the clotting process, to soak up blood, plasma and other fluids exuded from the wound, to provide pain relieving effect (including a placebo effect), to debride the wound, to protect the wound from infection and mechanical damage, and to promote healing through granulation and epithelialization.

The following list of commercial dressings includes those that may be employed in accordance with the present disclosure: Acticoat, Acticoat 7, Actisorb Silver 220, Algisite M, Allevyn, Allevyn Adhesive, Allevyn Cavity, Allevyn Compression, Allevyn Heel, Allevyn Sacrum, Allevyn cavity wound dressing, Aquacel, Aquacel AG, Aquacel ribbon, Bactigras, Biatain Adhesive, Bioclusive, Biofilm, Blenderm, Blue line webbing, Bordered Granuflex, Calaband, Carbonet, Cavi-care, Cellacast Xtra, Cellamin, Cellona Xtra, Cellona elastic, Chlorhexitulle, Cica-Care, Cliniflex odour control dressing, Clinisorb odour control dressing, Coban, Coltapaste, Comfeel Plus, Comfeel Plus pressure relieving dressing, Comfeel Plus transparent dressing, Comfeel Plus ulcer dressing, Comfeel seasorb dressing, Comfeel ulcer dressing, Contreet Non-Adhesive, Crevic, Cutinova Hydro, Cutinova Hydro Border, Debrisan absorbent pad, Debrisan beads, Debrisan paste, Delta-Cast Black Label, Delta-Cast conformable, Delta-Lite S, Duoderm extra thin, Durapore, Elastocrepe, Elset/Elset 'S', Flamazine, Fucidin Intertulle, Geliperm granulated gel, Geliperm sheet, Granuflex (Improved formulation), Granuflex extra thin, Granugel, Gypsona, Gypsona S, Hypafix, Icthaband, Icthopaste, Inadine, Intrasite Gel, Iodoflex, Iodosorb, Iodosorb ointment, Jelonet, K-Band, K-Lite, K-PLUS, Kaltocarb, Kaltostat, Kaltostat Fortex, Kaltostat cavity dressing, LarvE (Sterile Maggots), Lestreflex, Lyofoam, Lyofoam 'A', Lyofoam C, Mefix, Melolin, Mepiform, Mepilex, Mepilex AG, Mepilex Border, Mepilex Border Lite, Mepilex Border Sacrum, Mepilex Heel, Mepilex Lite, Mepilex Transfer, Mepitac, Mepitel, Mepore, Mepore Pro, Mesitran, Mesorb, Metrotop, Microfoam, Micropore, Opsite Flexigrid, Opsite IV 3000, Orthoflex, Oxyzyme, Paratulle, Polymem, Polymem Island & Shapes, Polymem Max, Polymem Silver, ProGuide, Profore, Promogran, Quinaband, Release, Scotchcast Plus, Scotchcast Softcast, Serotulle, Setopress, Silastic foam, Silicone N-A, Sofra-Tulle, Sorbsan, Sorbsan Plus, Sorbsan SA, Sorbsan Silver, Sorbsan Silver Plus Self Adhesive, Spenco 2nd Skin, Spyroflex, Spyrosorb, Tarband, Tegaderm, Tegaderm Plus, Tegagel, Tegapore, Tegasorb, Telfa, Tensopress, Tielle, Tielle Lite, Tielle Plus, Tielle Plus Borderless, Transpore, Unitulle, Veinoplast, Veinopress, Versiva, Vigilon, Viscopaste PB7, Xelma, and Zincaband.

A typical (sterile) dressing is one made of a film, foam, semi-solid gel, pad, gauze, or fabric. More particularly, sterile dressings are made of silicone, a fibrin/fibrinogen matrix, polyacrylamide, PTFE, PGA, PLA, PLGA, a polycaprolactone or a hyaluronic acid, although the number and type of materials useful in making dressings is quite large. Dressing may further be described as compression dressings, adherent dressing and non-adherent dressings.

Dressings may advantageously include other materials—active or inert. Such materials include gelatin, silver, cellulose, an alginate, collagen, a hydrocolloid, a hydrogel, a skin substitute, a wound filler, a growth factor, an antibody, a protease, a protease inhibitor, an antibacterial peptide, an adhesive peptide, a hemostatic agent, living cells, honey, nitric oxide, a corticosteroid, a cytotoxic drug, an antibiotic, an antimicrobial, an antifungal, an antiseptic, nicotine, an anti-platelet drug, an NSAID, colchicine, an anti-coagulant, a vasoconstricting drug or an immunosuppressive.

Wound dressings may also be part of a larger device, such as one that permits fixation of the dressing to a wound, such as an adhesive or a bandage. Dressings/devices may also include other features such as a lubricant, to avoid adhesion of the dressing to the wound, an absorber to remove seepage from the wound, padding to protect the wound, a sponge for absorbance or protection, a wound veil, an odor control agent, and/or a cover.

The isoxazole agent, or any other agent, may be applied to a dressing, or disposed in a dressing, by virtue of its introduction into or onto the dressing in a liquid, a salve, an ointment, a gel or a powder. Alternatively, the isoxazole agent or other agent may be added to a discrete element of a dressing (a sheet or film) that is included in the dressing during its manufacture.

Devices may also include a port, such as one providing operable connection between said sterile dressing and a tube, as well as a cover providing an airtight seal to or around a wound surface. Such embodiments are particularly useful in negative pressure wound therapy methods and devices.

B. Sutures

A surgical suture is a medical device used to hold body tissues together after an injury or surgery. It generally a length of thread, and it attached to a needle. A number of different shapes, sizes, and thread materials have been developed over time. The present disclosure envisions the coating or impregnating of sutures with isoxazole compounds.

The first synthetic absorbable was based on polyvinyl alcohol in 1931. Polyesters were developed in the 1950s, and later the process of radiation sterilization was established for catgut and polyester. Polyglycolic acid was discovered in the 1960's and implemented in the 1970s. Today, most sutures are made of synthetic polymer fibers, including the absorbables polyglycolic acid, polylactic acid, and polydioxanone as well as the non-absorbables nylon and polypropylene. More recently, coated sutures with antimicrobial substances to reduce the chances of wound infection have been developed. Sutures come in very specific sizes and may be either absorbable (naturally biodegradable in the body) or non-absorbable. Sutures must be strong enough to hold tissue securely but flexible enough to be knotted. They must be hypoallergenic and avoid the "wick effect" that would allow fluids and thus infection to penetrate the body along the suture tract.

All sutures are classified as either absorbable or non-absorbable depending on whether the body will naturally degrade and absorb the suture material over time. Absorbable suture materials include the original catgut as well as the newer synthetics polyglycolic acid (Biovek), polylactic acid, polydioxanone, and caprolactone. They are broken down by various processes including hydrolysis (polyglycolic acid) and proteolytic enzymatic degradation. Depending on the material, the process can be from ten days to eight weeks. They are used in patients who cannot return for suture removal, or in internal body tissues. In both cases, they will hold the body tissues together long enough to allow healing, but will disintegrate so that they do not leave foreign material or require further procedures. Occasionally, absorbable sutures can cause inflammation and be rejected by the body rather than absorbed.

Non-absorbable sutures are made of special silk or the synthetics polypropylene, polyester or nylon. Stainless steel wires are commonly used in orthopedic surgery and for sternal closure in cardiac surgery. These may or may not have coatings to enhance their performance characteristics. Non-absorbable sutures are used either on skin wound closure, where the sutures can be removed after a few weeks, or in stressful internal environments where absorbable sutures will not suffice. Examples include the heart (with its constant pressure and movement) or the bladder (with adverse chemical conditions). Non-absorbable sutures often cause less scarring because they provoke less immune response, and thus are used where cosmetic outcome is important. They must be removed after a certain time, or left permanently.

In recent years, topical cyanoacrylate adhesives (liquid stitches") have been used in combination with, or as an alternative to, sutures in wound closure. The adhesive remains liquid until exposed to water or water-containing substances/tissue, after which it cures (polymerizes) and forms a flexible film that bonds to the underlying surface. The tissue adhesive has been shown to act as a barrier to microbial penetration as long as the adhesive film remains intact. Limitations of tissue adhesives include contraindications to use near the eyes and a mild learning curve on correct usage.

Cyanoacrylate is the generic name for cyanoacrylate based fast-acting glues such as methyl-2-cyanoacrylate, ethyl-2-cyanoacrylate (commonly sold under trade names like Superglue™ and Krazy Glue™) and n-butyl-cyanoacrylate. Skin glues like Indermil® and Histoacryl® were the first medical grade tissue adhesives to be used, and these are composed of n-butyl cyanoacrylate. These worked well but had the disadvantage of having to be stored in the refrigerator, were exothermic so they stung the patient, and the bond was brittle. Nowadays, the longer chain polymer, 2-octyl cyanoacrylate, is the preferred medical grade glue. It is available under various trade names, such as LiquiBand®, SurgiSeal®, FloraSeal®, and Dermabond®. These have the advantages of being more flexible, making a stronger bond, and being easier to use. The longer side chain types, for example octyl and butyl forms, also reduce tissue reaction.

C. Negative Pressure Wound Therapy

Negative pressure wound therapy (NPWT), also known as topical negative pressure, sub-atmospheric pressure dressings or vacuum sealing technique, is a therapeutic technique used to promote healing in acute or chronic wounds, fight infection and enhance healing of burns. A vacuum source is used to create sub-atmospheric pressure in the local wound environment. The wound is sealed to prevent dehiscence with a gauze or foam filler dressing, and a drape and a vacuum source applies negative pressure to the wound bed with a tube threaded through the dressing. The vacuum may be applied continuously or intermittently, depending on the type of wound being treated and the clinical objectives. Intermittent removal of used instillation fluid supports the cleaning and drainage of the wound bed and the removal of infectious material. In the instant case, NPWT can be used in conjunction with administration of an isoxazole.

NPWT has multiple forms which mainly differ in the type of dressing used to transfer NPWT to the wound surface, and include both gauze and foam. Gauze has been found to effect less tissue ingrowth than foam. The dressing type depends on the type of wound, clinical objectives and patient. For pain sensitive patients with shallow or irregular wounds, wounds with undermining or explored tracts or tunnels, and for facilitating wound healing, gauze may be a better choice for the wound bed, while foam may be cut easily to fit a patient's wound that has a regular contour and perform better when aggressive granulation formation and wound contraction is the desired goal. The technique is often used with chronic wounds or wounds that are expected to present difficulties while healing (such as those associated with diabetes or when the veins and arteries are unable to provide or remove blood adequately).

VIII. KITS

For use in the applications described herein, kits are also within the scope of the disclosure. Such kits can comprise a carrier, package or container that is compartmentalized to receive one or more containers such as vials, tubes, and the like, each of the container(s) comprising one of the separate elements to be used in the method, in particular, an isoxazole or MRTF-A inhibitor. The kit of the disclosure will typically comprise the container described above and one or more other containers comprising materials desirable from a commercial end user standpoint, including buffers, diluents, filters, needles, syringes, and package inserts with instructions for use. In addition, a label can be provided on the container to indicate that the composition is used for a specific therapeutic application, and can also indicate directions for either in vivo or in vitro use, such as those described above. Directions and or other information can also be included on an insert which is included with the kit.

IX. EXAMPLES

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. The present examples, along with the methods described herein are presently representative of particular embodiments, are exemplary, and are not intended as limitations on the scope of the disclosure. Changes therein and other uses which are encompassed within the spirit of the disclosure as defined by the scope of the claims will occur to those skilled in the art.

Example 1—Materials and Methods

Cell Culture and Transfection.

Mouse NIH/3T3 and human BR5 fibroblasts were grown as in DMEM supplemented with 10% BCS or FBS at 37° C. in a 5% CO2 incubator as previously described (Rhee et al., 2007). Primary mouse tail tip fibroblasts (TTFs) were isolated from 6- to 8-wk-old myocardin-related transcription factor (MRTF)-A−/− or wild-type littermates and cultured in DMEM supplemented with 10% FBS, nonessential amino acids, L-glutamine, and sodium pyruvate as described previously (Song et al., 2012). Once TTFs became confluent, cells were frozen in 10% DMSO containing growth media for future use before passage 3.

NIH/3T3 cells were transfected with 10 ng empty flag or flag epitope-tagged MRTF-A vector along with 100 ng smooth muscle a-actin (SMA), atrial natriuretic factor (ANF), SM22, or skeletal actin (SKA) luciferase reporter and 20 ng of β-galactosidase (β-gal) expression construct using Fugene6 (Roche). Plasmid DNA content was kept constant using empty pcDNA3.1-flag. BR5, NIH/3T3, or TTF cells were infected with adenovirus directing the expression of flag-MRTF-A, HA-MRTF-A, or β-gal as control at the multiplicity of infection (MOI) noted in the text. For experiments using chemical compounds or growth factors, cells were cultured in serum-free media (SF) for 24 h before treatment, followed by an additional 24- to 48-hr incubation in SF media treated with TGF-β1 (10 ng/mL, R&D Systems) solubilized in 4 mM HCl/1% BSA/PBS or isoxazole (20 µM) solubilized inDMSO.

Immunocytochemistry.

Cells were treated with the indicated factor for 24 h before fixation with methanol at −20° C. for 10 min. Indirect immunofluorescence was performed by incubating with the following primary antibodies at 4° C. overnight: mouse monoclonal Cy3-conjugated anti-SMA antibody (Sigma, clone 1A4, 1:200) and rabbit monoclonal anti-HA antibody (Cell Signaling, 1:300). A secondary goat Alexa Fluor 488-conjugated anti-rabbit IgG antibody (Invitrogen, 1:200) was used to visualize HA by incubation at RT for 1 hr. All images were captured using an Olympus IX81 confocal microscope.

Collagen Gel Contraction Assay.

BR5 cells (2×10$^5$) were infected with 25 MOI flag-MRTF-A, or GFP as control, for 48 hr and seeded in a 200 µL volume of 1.5 mg/mL rat tail collagen (BD Bioscience), essentially as described (Rhee et al., 2007). The BR5-containing collagen matrix was dispensed onto 12 mm diameter circles scored on the bottom of a 24-well tissue culture plate. Gels were allowed to polymerize for 1 hr. Gels for floating matrix contraction were then released from the tissue culture plastic followed by an overnight incubation in DMEM supplemented with 10% FBS to allow tension development. Gels for stressed matrix contraction were released from the tissue culture plastic after overnight in 10% FBS. Reduction of gel diameter in response to BSA control (5 mg/mL), FBS (10%), or PDGF (50 ng/mL) was calculated.

Western Blot Analysis.

Whole cell extracts were subjected to SDS/PAGE and immunoblotted onto PVDF membranes (Millipore) with the following antibodies at 4° C. overnight: mouse monoclonal anti-SMA (Sigma, clone 1A4, 1:1,000), rabbit polyclonal anti-SM22 (Abcam, 1:5,000), rabbit monoclonal Smad2/3 and phoshpho-Smad2/3 (Cell Signaling, 1:1,000), rabbit monoclonal Erk1/2 and phsopho Erk1/2 (Cell Signaling, 1:1,000), SRF (Santa Cruz, 1:1,000), rabbit monoclonal Vimentin (Abcam, 1:1,000), rabbit polyclonal Fsp1 (S100a4, 1:1,000), mouse monoclonal anti-FlagM2 (Sigma, 1:5,000), and mouse monoclonal anti-GAPDH (Millipore, 1:30,000). Secondary goat HRP-conjugated anti-mouse or -rabbit IgG antibody (BioRad) was incubated for 1 hr at room temperature and developed with luminol reagent (Santa Cruz).

RNA Isolation and Analysis.

Total RNA was isolated from cell cultures and tissue samples using TRIzol reagent (Invitrogen), and cDNA was generated using iScript cDNA Synthesis Kit (BioRad) following the manufacturer's protocol. Gene expression was examined using standard RT-PCR methods and visualized by gel electrophoresis or qRT-PCR methods with iQ SYBR Green Supermix (BioRad). Primer sequences, annealing temperature, and cycle numbers are listed in Table 1.

Mouse Lines and Wound-Healing Assay.

All experiments using animals were previously approved by the University Committee on Animal Resources at University of Rochester and the Institutional Animal Care and Use Committee at the University of Texas Southwestern Medical Center. The MRTF-A$^{-/-}$ mouse line used in this study has been previously reported and is kept on a C57Bl6 background (Li et al., 2006). Wild-type C57BL6 mice were obtained from the Jackson Laboratories. Wound-healing assays were performed as previously reported (Dioufa et al., 2010). Briefly, mice were shaved down the back and wiped with betadine followed by full thickness incision with a biopsy punch (4 mm) Two biopsies were performed per mouse, and care was taken to assure equal skin tension for all wounds. Isoxazole (ISX) (20 µM in PBS) or an equal concentration of DMSO was applied to each mouse twice per day in an ~50-µL volume for 7 d. At the terminus of the study, wounds and control skin were excised and frozen in liquid nitrogen for RNA and protein isolation or fixed for histology.

Histology.

All samples were fixed in 4% paraformaldehyde, processed, paraffin-embedded, sectioned at 5-µm thickness, and stained for H&E or Masson's trichrome. For SMA immunofluorescence, sections were incubated with anti-SMA-Cy3 antibody (1:200) at 4° C. overnight. For Ki-67 detection, sections were pressure-cooked in antigen retrieval buffer (DAKO, pH 6.0) for 20 min and then incubated with rat anti-KI-67 antibody (DAKO, clone TEC-3, 1:500) at 4° C. overnight. Sections were then incubated with secondary biotinylated rabbit anti-rat IgG antibody (DAKO, 1:200) and ABC complex (Vector), each for 30 min at room temperature and developed with diaminobenzidine peroxidase substrate (Vector) for 10 min. Wounds were imaged using a dissecting scope or an Olympus IX81 confocal microscope and analyzed with National Institutes of Health ImageJ.

Data and Statistical Analysis.

Results are presented as the mean+/−SEM. Statistical differences were determined by a Student's two-tailed t-test with unequal variance or a one or two-way analysis of variance (ANOVA) with Tukey's post-hoc test, as needed. Significance was considered as p<0.05.

Example 2—Results

MRTF-A Contributes to Myofibroblast Differentiation and Contractility.

Figure 1C:
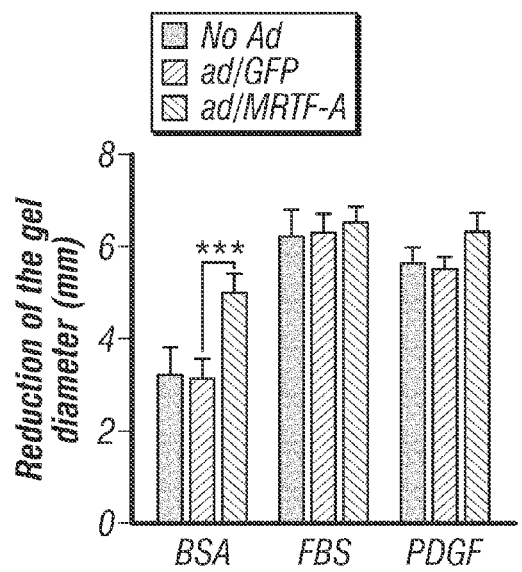

MRTF-A is broadly expressed and promotes the expression of genes encoding components of the actin cytoskeleton. Using cultured human dermal fibroblasts (BR5) suspended in a collagen solution, the inventors sought to probe the function of MRTFA in fibroblast contractility and myofibroblast differentiation. The fibroblast phenotype varies depending upon whether cells are grown in a collagen matrix that is floating or attached. Contraction of floating matrices results in mechanically relaxed tissue with cells that display the morphological and proliferative features of dermis (Grinnell & Petroll 2010). Contraction can be stimulated by addition of growth factors such as fetal bovine serum (FBS) or PDGF (Grinnell & Petroll 2010). Overexpression of MRTF-A by adenoviral delivery stimulated matrix contraction of BR5 fibroblasts compared to uninfected cells or cells infected with GFP-expressing adenovirus as a control (FIGS. 1A and 1C). The extent of contraction in response to MRTFA expression was approximately equivalent to that observed upon stimulation with FBS or PDGF (FIGS. 1A and 1C).

Figure 1D:
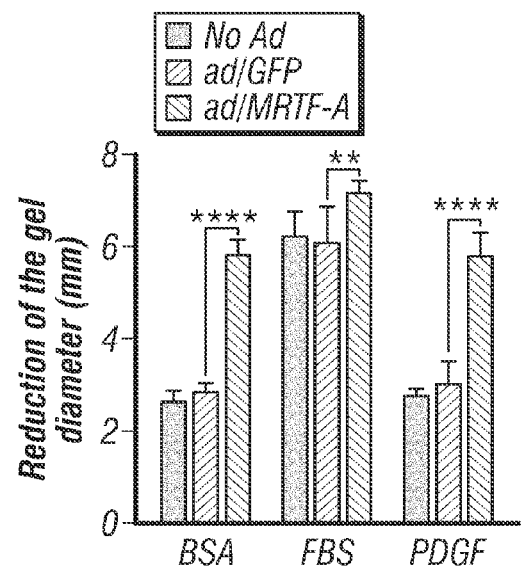

Stressed matrix contraction reflects active shortening by cells that are spread, exhibit stress fibers, and are well-adhered to the restrained matrix, in a process that can be stimulated by FBS, but not PDGF. Adhered collagen matrices develop into a stressed tissue resembling that of granulation tissue. Cell shortening was potently stimulated by forced expression of MRTF-A under all conditions tested (FIGS. 1B and 1D). These data suggest that MRTFA stimulates the myofibroblast phenotype, enhancing constitutive matrix remodeling and cell shortening.

Figure 2A:
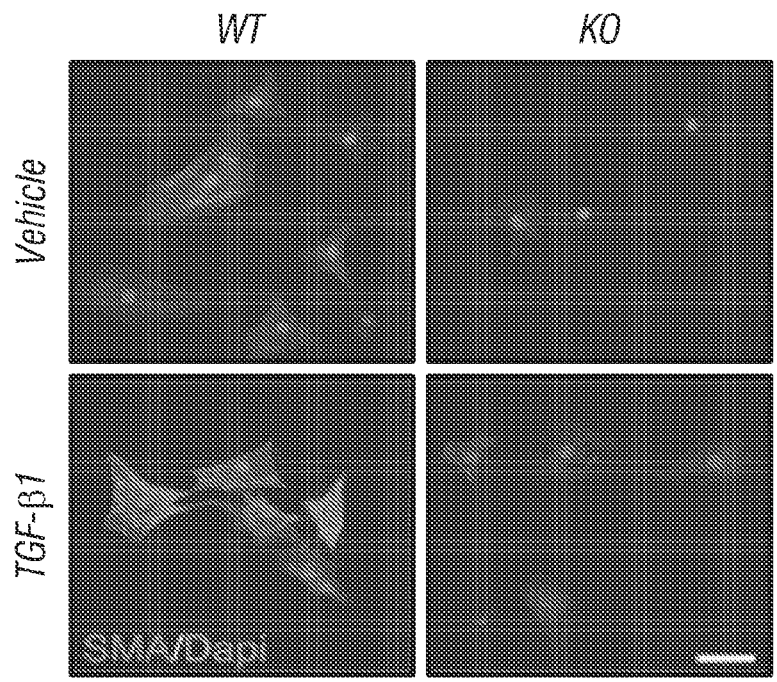
FIGS. 2A-D. MRTF-A is required for TGF-β1-induced contractile gene expression and stress fiber formation. Tail tip dermal fibroblasts isolated from MRTFAKO mice and WT littermates were serum-starved prior to treatment with TGF-β1 or vehicle for 48 hrs.
Figure 2B:
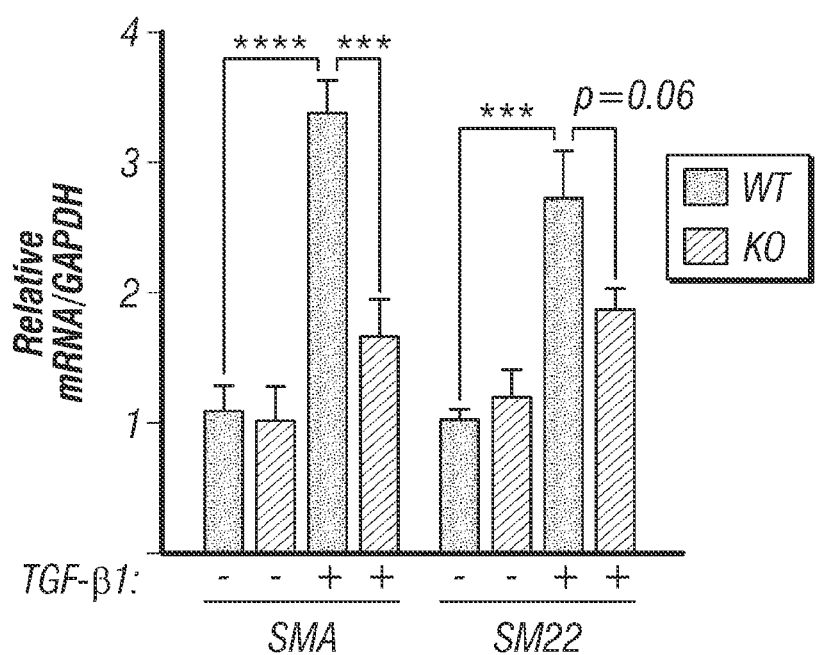
Figure 2C:
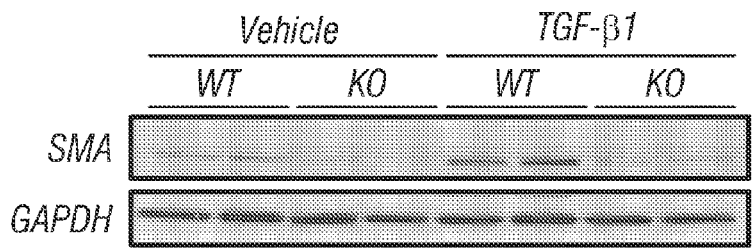
Figure 2D:
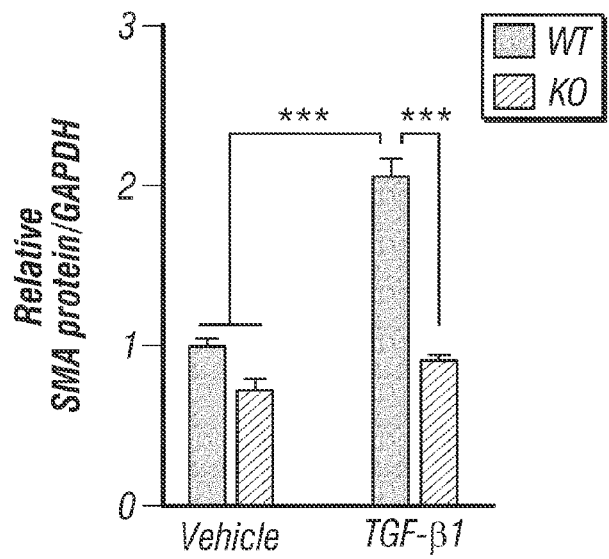

The inventors next asked whether MRTF-A is required for the process of myofibroblast differentiation, using tail tip fibroblasts (TTFs) isolated from MRTF-A knockout (KO) mice and WT littermates. When grown in culture, fibroblasts respond to TGF-β1 stimulation by adopting an elongated morphology and producing SMA-positive stress fibers (FIG. 2A). MRTF-A-deficient fibroblasts did not display an enrichment of SMA-positive stress fibers as observed in WT fibroblasts treated with TGF-β1 (FIG. 2A). Furthermore, the expression of genes encoding SMC contractile proteins (SMA and SM22) in response to TGF-β1 stimulation was blunted in MRTF-A-deficient TTFs as demonstrated by qPCR and Western blot (FIGS. 2B-D). Because MRTFA KO fibroblasts continue to express MRTF-B, it is likely that the residual expression of SMA in KO cells reflects MRTF-B redundancy or MRTF independent pathways.

Isoxazole Promotes MRTF-A-Dependent SMA Reporter Activation.

Figure 3A:
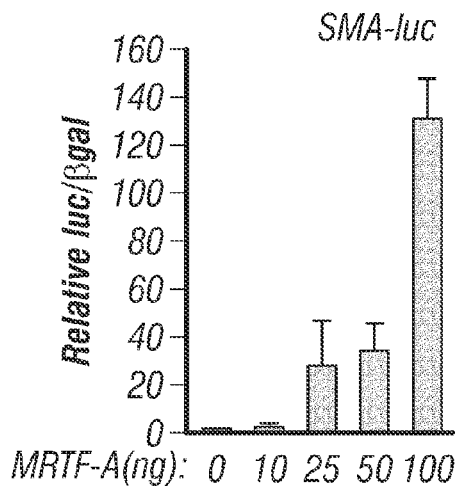
FIGS. 3A-F. ISX stimulates MRTF-A-dependent promoter activity. NIH/3T3 mouse fibroblasts were cotransfected with (FIG. 3A) 0-100 ng of MRTF-A or empty vector and 100 ng of SMA promoter-controlled luciferase construct to confirm promoter activation.
Figure 3B:
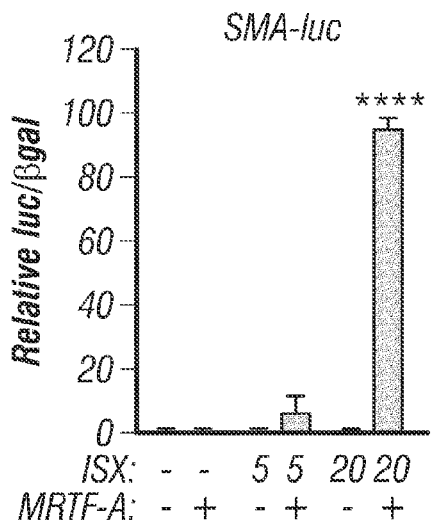
Figure 3C:
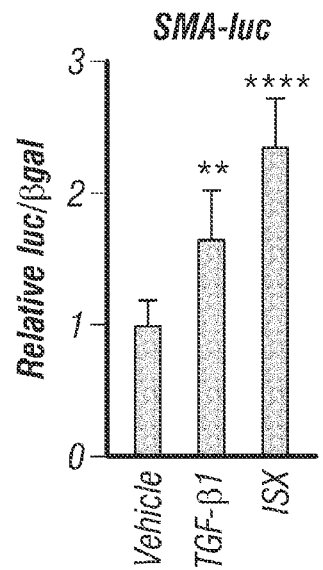

To examine the potential to pharmacologically manipulate myofibroblast differentiation, the inventors sought to identify molecules capable of modulating MRTF-A-dependent SMA expression, as a surrogate marker of the contractile phenotype. The inventors utilized a luciferase reporter controlled by ~125 nucleotides of the SMA promoter (SMA-luc) in NIH/3T3 fibroblasts, which provided a faithful readout of CArG-dependent MRTF-A activity (FIG. 3A). Using this approach, they screened ~300 compounds previously shown to promote cardiac and neural progenitor cell differentiation (27, 29). N-cyclopropyl-5-(thiophen-2-yl)-isoxazole-3-carboxamide (isoxazole or ISX) displayed a dose-dependent stimulation of SMA-luc upon forced expression of a minimal amount of MRTF-A (FIG. 3B). Isoxazole consistently stimulated reporter activity ~10-50 fold (at 20 μM), compared with MRTFA alone, and enhanced basal SMA-luc expression to an extent similar to or greater than that of TGF-β1 (FIG. 3C).

Figure 3D:
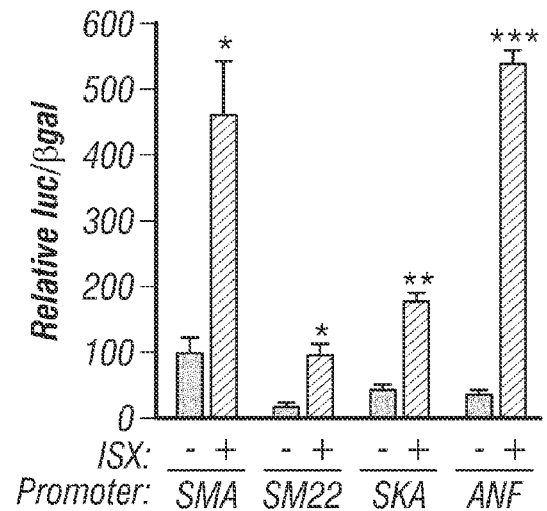
Figure 3E:
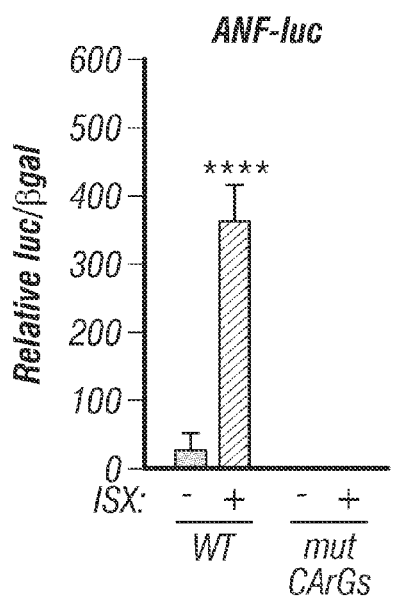
Figure 3F:
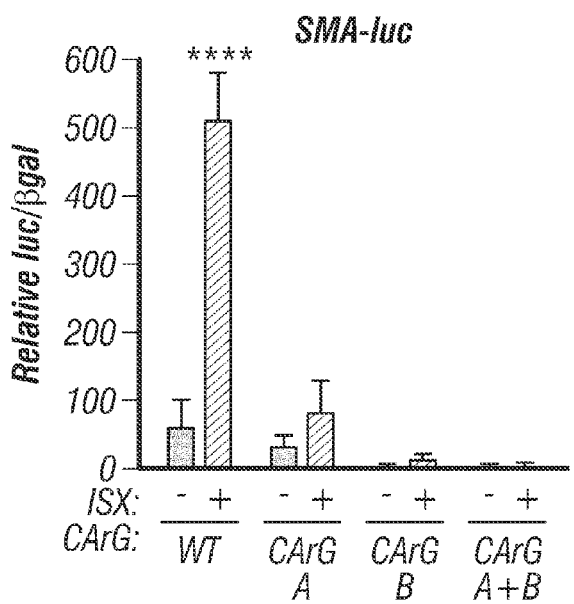
Figure 4A:
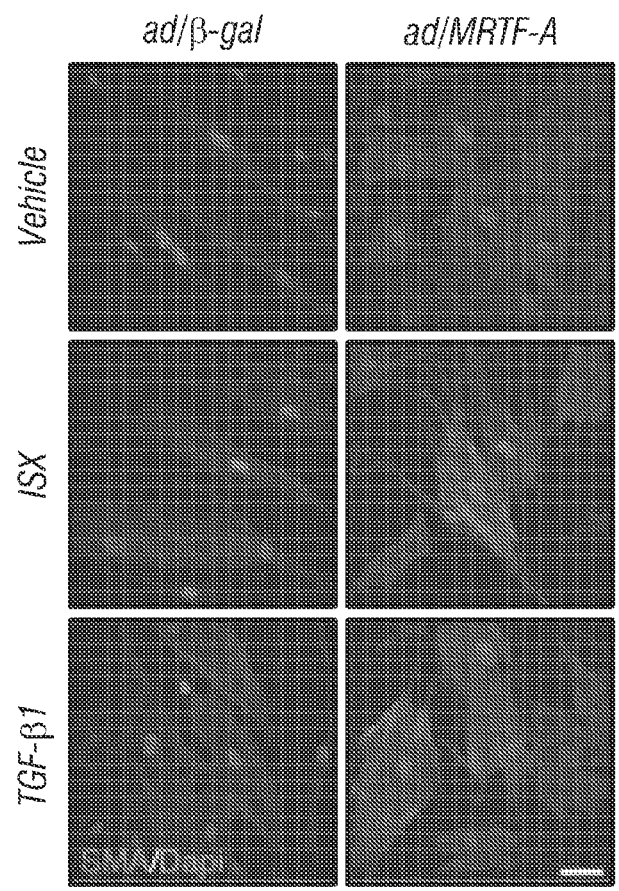
Figure 4B:
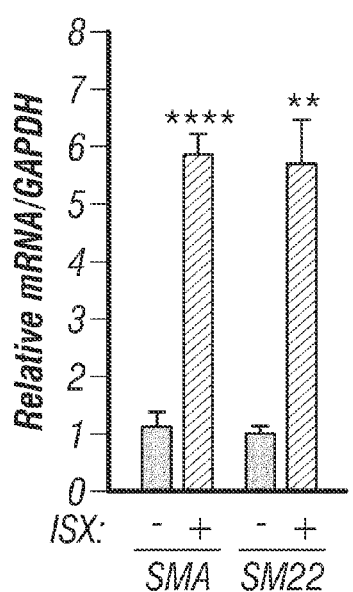
Figure 4C:
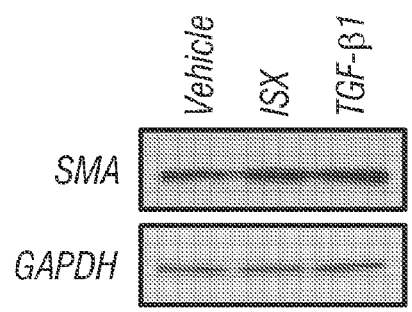

To directly analyze the influence of isoxazole on MRTF-A activity and myofibroblast differentiation, the inventors examined various CArG-dependent reporter constructs. In addition to SMA-luc, isoxazole stimulated MRTF-A-dependent luciferase reporters controlled by the SM22, skeletal α-actin (SKA), and atrial natriuretic factor (ANF) promoters (FIG. 3D) in the presence of an intermediate dose of exogenous MRTF-A. Point mutations in the CArG elements of the ANF and SMA promoters abrogated their responsiveness to isoxazole (FIGS. 3E-F). These data suggest the induction of smooth muscle contractile gene expression by isoxazole occurs via a CArG and SRF/MRTF-A-dependent mechanism. Isoxazole induces endogenous MRTF-A targets and the myofibroblast phenotype. Since isoxazole displayed such robust activity in a reporter assay, the inventors examined its effect on endogenous gene expression. Indeed, isoxazole treatment of BR5 fibroblasts induced morphological changes and the generation of SMA-positive stress fibers to a similar extent to that of TGF-β1 (FIG. 4A). Likewise, isoxazole resulted in a significant enrichment of SMA and SM22 mRNA levels as demonstrated by qRT-PCR (FIG. 4B), and a corresponding increase in SMA protein (FIG. 4C).

In order to determine whether MRTF-A was required for isoxazole-dependent SMA enrichment, the inventors isolated TTFs from MRTF-A KO and WT littermates. Isoxazole treatment stimulated the expression of SMA protein in WT but not in MRTFA KO fibroblasts (FIGS. 4D-E). These observations reveal a physiological response to MRTF-A and isoxazole in stimulation of the SMC contractile program and dermal myofibroblast differentiation.

Isoxazole Regulates MRTF-A/SRF Stability and Activity.

Figure 5B:
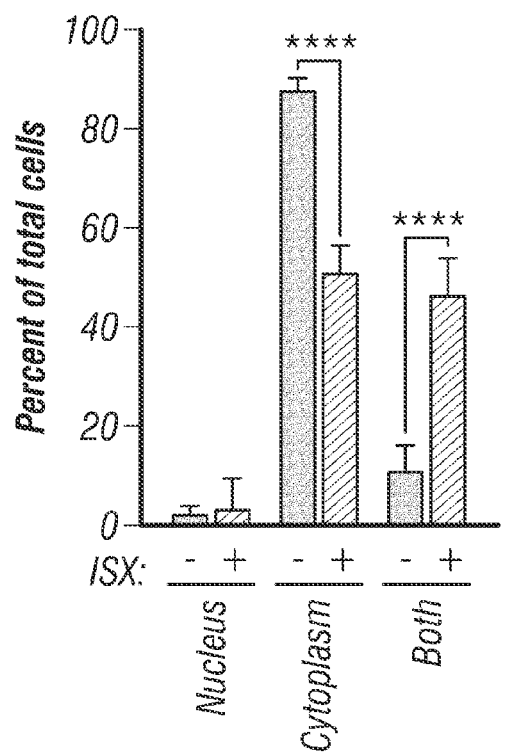
Figure 5C:
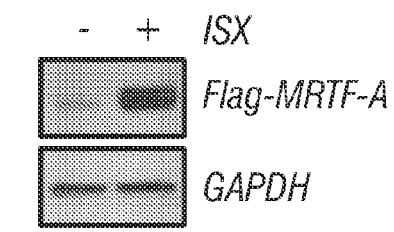
Figure 5D:
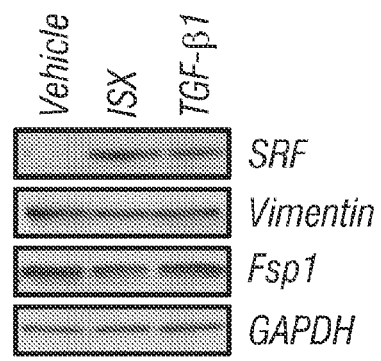
Figure 8:
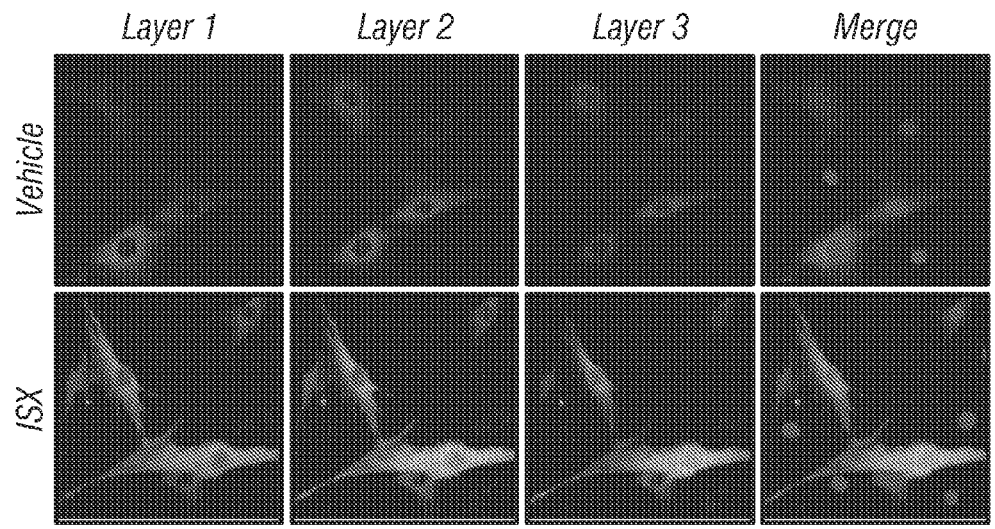
FIG. 8. ISX promotes MRTF-A enrichment and nuclear accumulation. BR5 human dermal fibroblasts were infected with HA-MRTF-A and treated with vehicle or ISX for 24 h Immunofluorescence for HA (green) or DAPI (blue, nuclei) demonstrates MRTF-A accumulation and nuclear localization. Selected images from various levels taken from a confocal Z-stack at lower (layer 1), midcell (layer 2), and upper (layer 3).
Figure 9:
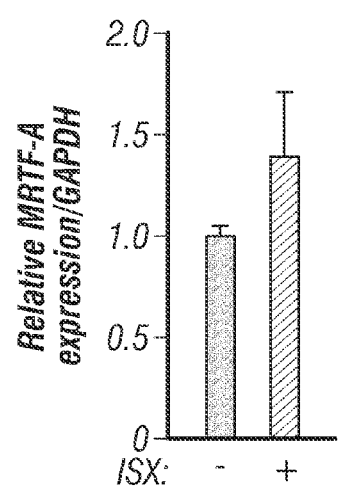
FIG. 9. MRTF-A mRNA levels are unchanged by ISX. NIH3T3 cells infected with HA-MRTF-A (25 MOI) and treated with ISX or vehicle. MRTF-A mRNA levels were analyzed using qRT-PCR and normalized to GAPDH.

To further probe the mechanism whereby isoxazole promotes MRTF-A target gene expression, the inventors examined the possible effects of this compound on MRTF-A protein function. Because MRTF-A activity is regulated at the level of nuclear localization, they first used an epitope-tagged MRTF-A construct to examine subcellular localization in response to isoxazole treatment. The inventors observed a striking accumulation of MRTF-A protein in the presence of isoxazole, which was accompanied by an increase in the number of cells displaying nuclear MRTF-A (FIGS. 5A-B and FIG. 8). Nuclear accumulation under these conditions appeared to stem from increased levels of MRTF-A protein, as the inventors did not observe an increased number of cells displaying MRTF-A exclusively in the nucleus (FIG. 5B). Western analysis revealed the enrichment of both MRTF-A (FIG. 5C) and SRF (FIG. 5D) in isoxazole treated cells, while transcript levels were not altered (FIG. 9). In contrast, isoxazole did not increase the level of the pan-fibroblast markers fibroblast-specific protein-1 (Fsp1, S100a4) and vimentin (FIG. 5D), suggesting a relatively specific effect on SRF/MRTF protein.

Figure 5E:
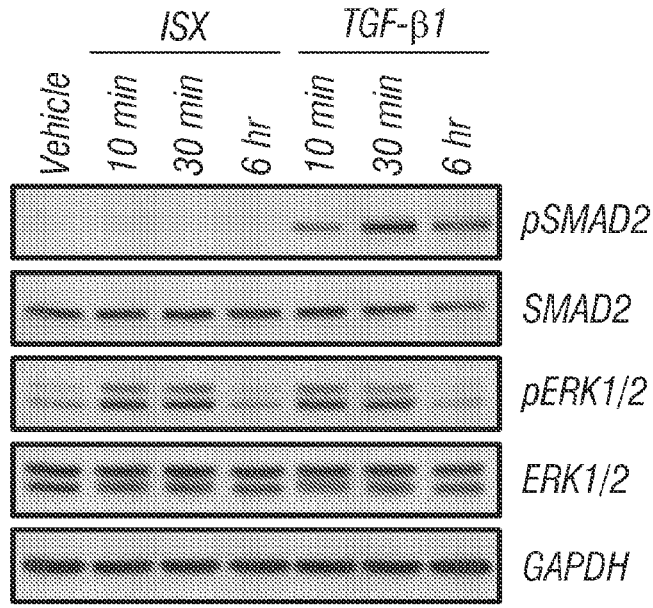

The inventors next examined the potential influence of isoxazole on signal transduction pathways that affect the fibroblast phenotype and might impinge upon SRF/MRTF activity. Isoxazole treatment did not affect the phosphorylation of Smad2/3 (FIG. 5E), further suggesting isoxazole does not promote canonical TGF-β-Smad signaling. Isoxazole treatment did, however, lead to the rapid and transient phosphorylation of extracellular-signal-regulated kinases Erk1/2 (FIG. 5E) (16).

Isoxazole Promotes Wound Healing In Vivo.

Figure 6A:
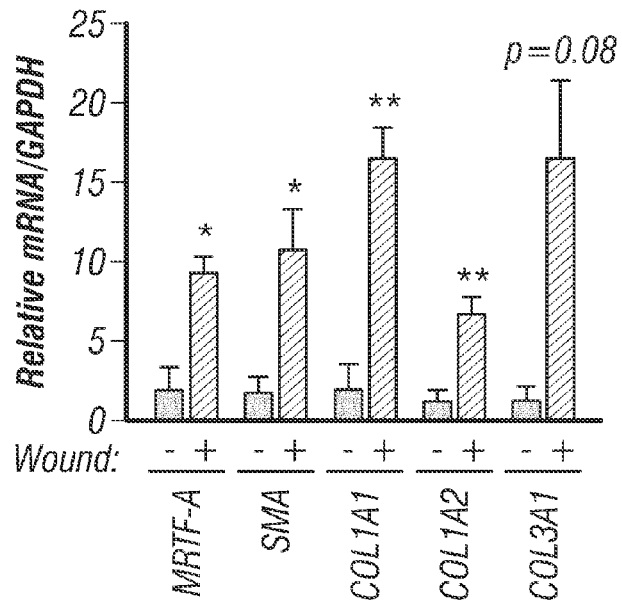
FIGS. 6A-E. ISX promotes wound closure in vivo. WT mice were subjected to full thickness cutaneous punch biopsies (n=4).

Given the role of myofibroblasts in wound healing and the potent stimulation of MRTF-A activity and myofibroblast gene expression by isoxazole, the inventors examined whether isoxazole could promote wound healing in vivo. To validate the potential involvement of the MRTF-SRF axis in healing wounds, they evaluated MRTF-A and SMC contractile gene expression in biopsies from WT mice seven days post-injury. Dermal wounds displayed enrichment of the myofibroblast marker SMA and various collagens (COL1A1, COL1A2, and COL3A1) as well as MRTF-A compared to dermis from uninjured controls (FIG. 6A).

Figure 6B:
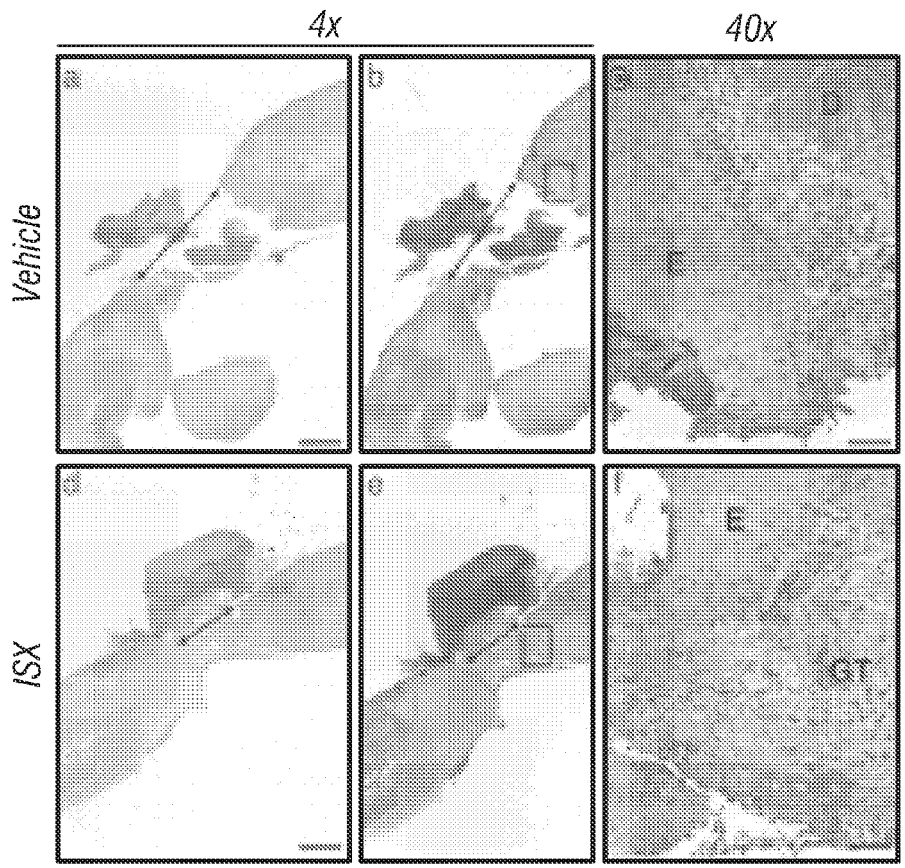
Figure 6C:
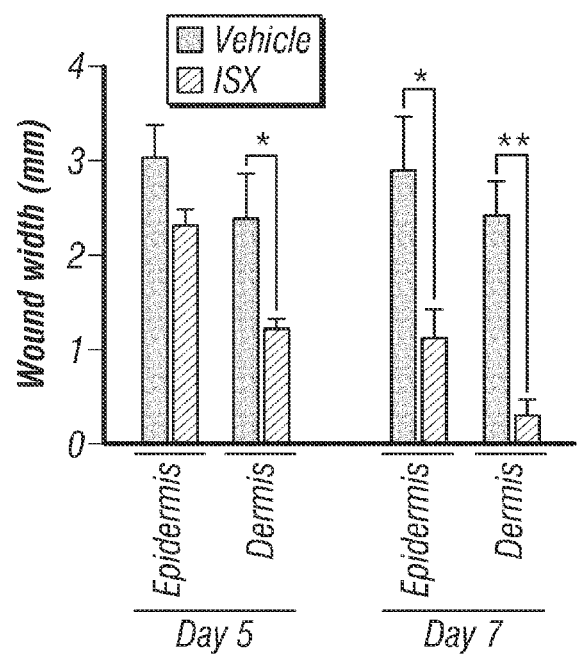
Figure 6E:
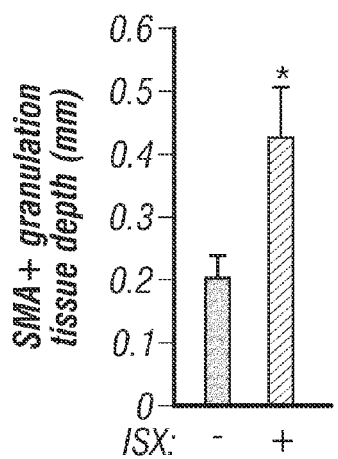
Figure 6D:
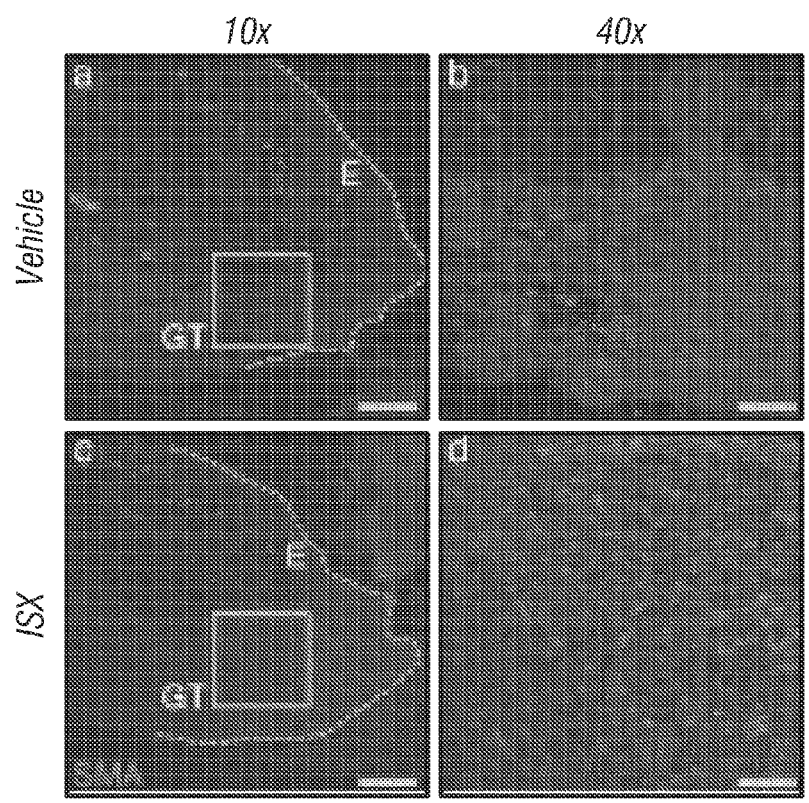
Figure 10:
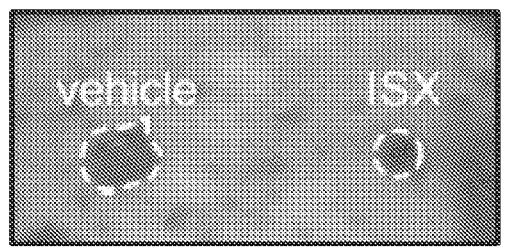
FIG. 10. Effect of ISX on wound healing. Wild-type mice were subjected to two wounds; one wound was treated with 20 μM ISX twice per day and the second with DMSO (vehicle) as an internal control. Wound was imaged 7 d following punch biopsy.
Figure 11:
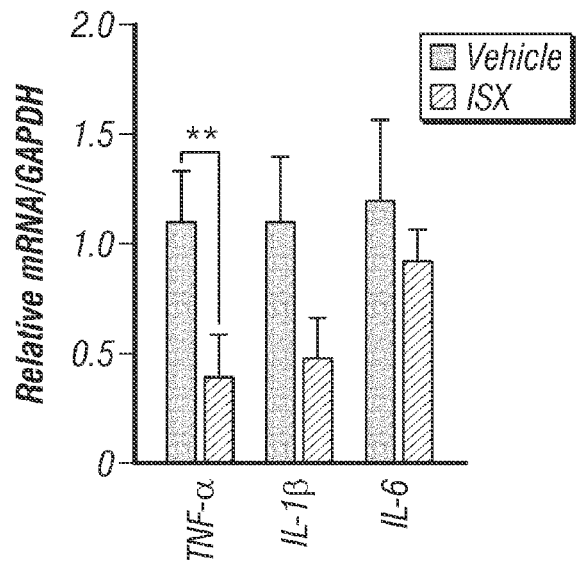
FIG. 11. Inflammatory marker analysis in ISX-treated wounds. Biopsies were isolated from wounds treated with ISX (20 μM) or vehicle, two times per day for 7 d. qRT-PCR analysis of inflammatory markers (n=4, **P<0.01).
Figure 12:
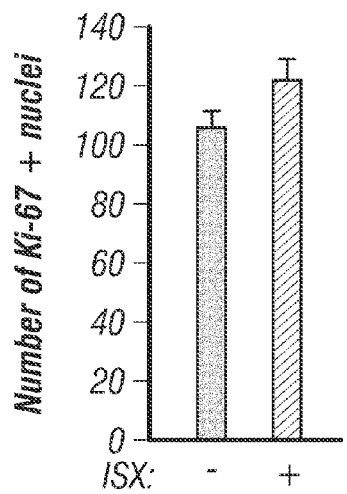
FIG. 12. Proliferation is not affected by ISX treatment of wounds. Number of Ki67-positive nuclei within the granulation tissue per field of view in ISX- or vehicle-treated wounds after 7 d.

To determine if isoxazole could promote wound healing, WT mice were subjected to two full thickness cutaneous wounds; one wound was treated with isoxazole (20 μM) twice per day for seven days while the second wound was treated with vehicle, serving as an internal control to limit inter-mouse variability. Isoxazole-treated wounds were smaller (FIG. 10), and displayed a blunted immune response as measured by the reduction of the pro-inflammatory cytokine TNF-α (FIG. 11). Histological analysis seven days after injury revealed a much more compact wound with expanded and more cellularized granulation tissue upon isoxazole treatment (FIG. 6B), which was associated with a significant narrowing between the epithelial sheets (FIG. 6B). Quantification granulation tissue layer by five days after injury and a significantly smaller wound by seven days (FIG. 6C). Furthermore, immunofluorescent detection of SMA revealed qualitatively more staining in the granulation tissue of isoxazole-treated wounds (FIG. 6D), and the depth of SMA positive granulation tissue was significantly greater than that of control wounds (FIG. 6E), although the inventors did not observe alterations in cell proliferation seven days post-injury (FIG. 12). Taken together, these findings reveal that isoxazole promotes MRTF/SRF dependent myofibroblast differentiation in vitro and leads to the improvement of cutaneous wound healing.

TABLE 1

Primers used in this study

| Gene | Forward | Reverse |
|---|---|---|
| mus COL1A1 | TAGGCCATTGTGTATGCAGC (SEQ ID NO. 1) | ACATGTTCAGCTTTGTGGACC (SEQ ID NO. 2) |
| mus COL1A2 | AGCAGGTCCTTGGAAACCTT (SEQ ID NO. 3) | AAGGAGTTTCATCTGGCCCT (SEQ ID NO. 4) |
| mus COL3A1 | TAGGACTGACCAAGGTGGCT (SEQ ID NO. 5) | GGAACCTGGTTTCTTCTCACC (SEQ ID NO. 6) |
| mus GAPDH | CGTGCCGCCTGGAGAAAC (SEQ ID NO. 7) | TGGGAGTTGCTGTTGAAGTCG (SEQ ID NO. 8) |
| mus IL-1β | CTACAGGCTCCGAGATGAAC (SEQ ID NO. 9) | TTCTTCTTTGGGTATTGCTTGG (SEQ ID NO. 10) |
| mus IL6 | ACAAAGAAATGATGGATGCTACC (SEQ ID NO. 11) | GTATCTCTCTGAAGGACTCTGG (SEQ ID NO. 12) |
| mus MRTF-A | ACGAGGCGGTTACCATCAC (SEQ ID NO. 13) | GCAGACAGAGACAGGAGCAC (SEQ ID NO. 14) |
| mus MRTF-B | CGATAGCTCCAAGAAGCAGC (SEQ ID NO. 15) | TTTTCTGGTTGCTTCCCTCA (SEQ ID NO. 16) |
| mus MYOCD | AAGGTCCATTCCAACTGCTC (SEQ ID NO. 17) | CCATCTCTACTGCTGTCATCC (SEQ ID NO. 18) |
| mus SM22 | GACTGCACTTCTCGGCTCAT (SEQ ID NO. 19) | CCGAAGCTACTCTCCTTCCA (SEQ ID NO. 20) |
| mus SMA | GTTCAGTGGTGCCTCTGTCA (SEQ ID NO. 21) | ACTGGGACGACATGGAAAAG (SEQ ID NO. 22) |
| mus SRF | CACCTACCAGGTGTCGGAAT (SEQ ID NO. 23) | GTCTGGATTGTGGAGGTGGT (SEQ ID NO. 24) |
| mus TNF-α | TCTTCTCATTCCTGCTTGTG (SEQ ID NO. 25) | ACTTGGTGGTTTGCTACG (SEQ ID NO. 26) |

PCR parameters: denature 95° C., 30 s; annealing 60° C., 30 s; extension 72° C., 30 s; 3×cycles.

TABLE 2

Antibodies used for Western blots in this study

| Antigen | Source | Host | Dilution |
|---|---|---|---|
| ERK1/2 | Cell Signaling | Rabbit | 1:5,000 |
| Phospho Erk1/2 | Cell Signaling | Rabbit | 1:5,000 |
| FlagM2 | Sigma | Mouse | 1:5,000 |
| GAPDH | Millipore | Mouse | 1:30,000 |
| S100a4 | Abcam | Rabbit | 1:500 |
| SMA | Sigma, clone 1A4 | Mouse | 1:1,000 |
| SMAD2/3 | Cell Signaling | Rabbit | 1:1,000 |
| Phospho-Smad2/3 | Cell Signaling | Mouse | 1:1,000 |
| SRF | Santa Cruz | Rabbit | 1:1,000 |
| Vimentin | Abcam | Rabbit | 1:5,000 |

Example 3—Discussion

Although it is well-accepted that resident fibroblasts contribute to the healing process in nearly every tissue examined, the molecular mechanisms that govern the phenotypic transformation of a quiescent fibroblast into a contractile myofibroblast and the precise role of this cell population in wound repair are poorly understood (Small 2012). In the current study, the inventors demonstrate that MRTF-A is a potent agonist of the myofibroblast phenotype. MRTF-A activates the smooth muscle contractile gene program, promotes SMA-positive stress fiber formation, and enhances fibroblast contractility in a collagen matrix. Furthermore, fibroblasts from MRTF-A KO mice display defective myofibroblast differentiation, demonstrating the involvement of MRTF-A in this process and confirming results of a previous study utilizing a siRNA knockdown approach (Crider et al., 2011).

Figure 7:
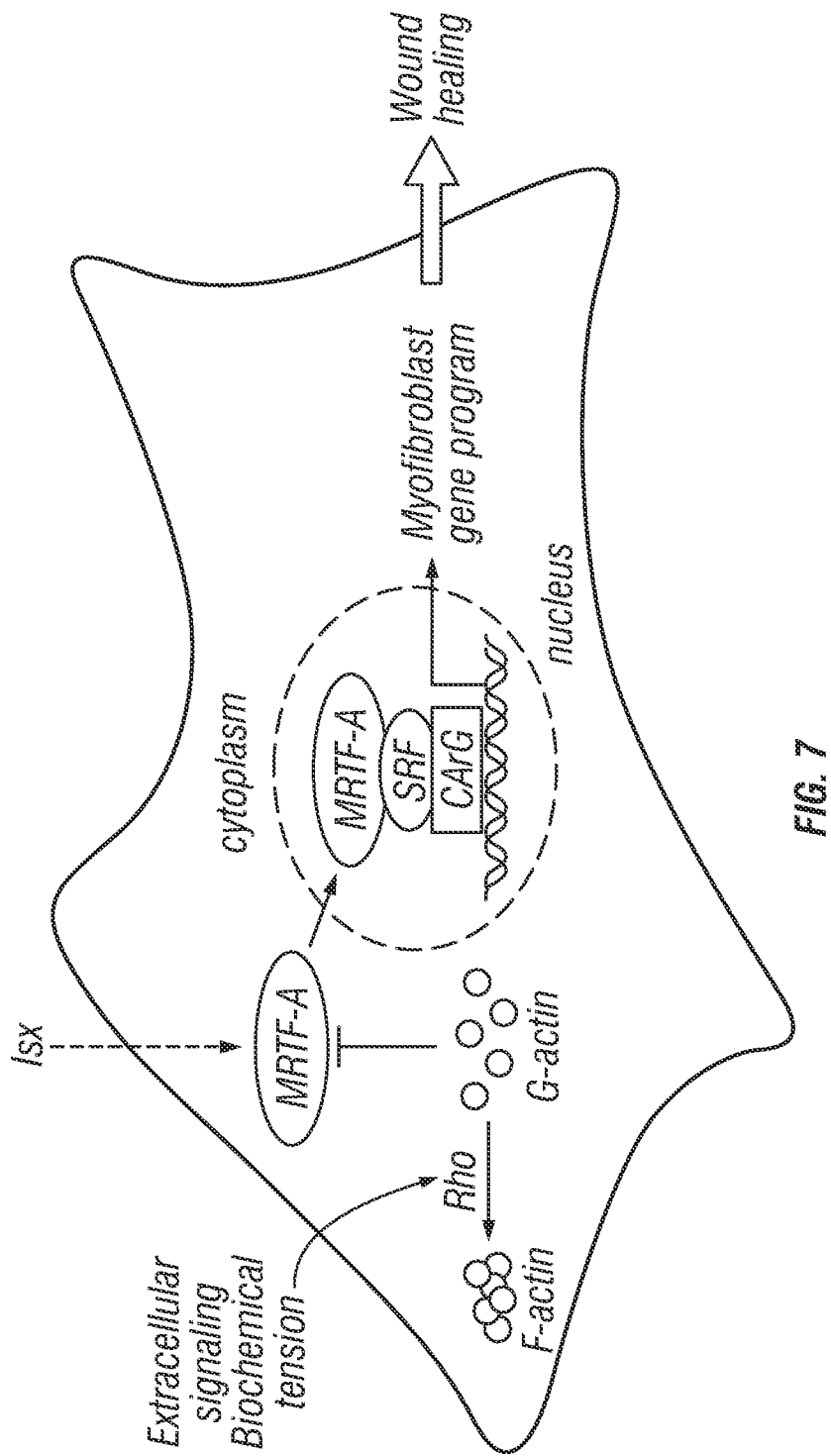
FIG. 7. ISX stimulates MRTF-mediated myofibroblast differentiation. Simplified view of the actions of MRTF-A and ISX during fibroblast differentiation. Mechanical stress or extracellular signals that stimulate Rho-ROCK dependent F-actin polymerization lead to MRTF-A nuclear translocation and activation of SRF target genes. ISX treatment leads to the accumulation of MRTF-A protein and stimulation of SRF target genes that promote the myofibroblast phenotype.

Using a SMA-luciferase reporter, the inventors devised a strategy to screen for factors that influence myofibroblast activation. They identified an isoxazole-ring containing analog, which stimulated the SMA promoter and induced the myofibroblast phenotype in an MRTF-A-dependent manner (FIG. 7). This method could potentially also identify MRTF-A-independent pathways, since the luciferase reporter construct used in this assay contains multiple regulatory elements in addition to the two CArG boxes, including a TGF-β/Smad response element and AP2 site (Cogan et al., 2002, Subramanian et al. 2004, Hautmann et al., 1997). Based on the finding that isoxazole does not affect Smad2/3 phosphorylation, and mutation of CArG boxes abolishes responsiveness to isoxazole, the phenotypic change elicited by isoxazole likely occurs via the promotion of MRTF/SRF activity. Importantly, a recent study utilizing a similar SMA-luc based screen identified the TRPC6 $Ca^{2+}$ channel as key agonist of TGF-β1/SRF-dependent myofibroblast differentiation and wound healing (Davis et al., 2012).

Isoxazole has been shown to activate the G-protein coupled receptor GPR68, leading to Ca2+ signaling (Russell et al., 2012), which could potentially couple to this pathway. Together, these studies support the conclusion that the MRTF-SRF regulatory axis plays a central role in myofibroblast differentiation. Interestingly, isoxazole induced the myofibroblast phenotype at least in part via stimulation of MRTF-A activity, likely reflecting the enrichment of MRTF-A protein. Levels of MRTF-A were significantly higher in isoxazole treated fibroblasts, which led to a greater proportion of cells displaying nuclear accumulation of MRTF-A. A previous study reported regulation of MRTF-A protein stability by the proteasome degradation pathway, suggesting the possibility that isoxazole might inhibit the ubiquitinproteasome system (Elberg et al. 2008).

The inventors also observed stimulation of Erk1/2 phosphorylation by isoxazole, implying the potential regulation of both the SRF-dependent growth response and contractile gene program (Wang et al., 2004). Indeed, phosphorylation of MRTF-A by Erk1/2 inhibits its nuclear localization (Muehlich et al., 2008), potentially explaining the inventors' observation that the majority of the stabilized MRTF-A remains in the cytoplasm. Recently, isoxazole analogs have been used to stimulate differentiation of adult cardiac progenitors and neural stem cells (Russell et al., 2012 and Schneider et al., 2008) and were shown to enhance insulin production by pancreatic beta cells (Dioum et al., 2011). It is not yet clear whether a common mechanism underlies these findings, although each response is associated with increased activity of key transcription factors. Isoxazole enhanced the phosphorylation and nuclear export of histone deacetylase 5 (HDAC5) in neural stem cells, thereby promoting transcriptional activation of myocyte enhancer factor-2 (MEF2) target genes (Schneider et al., 2008), and also stimulated p300 and cAMP response element binding protein (CBP) acetyl-transferase activity in pancreatic beta cells (Dioum et al., 2011). Of note, myocardin family proteins bind to and are stimulated by p300 and are repressed by HDAC activity (Cao et al., 2005).

Figure 13A:
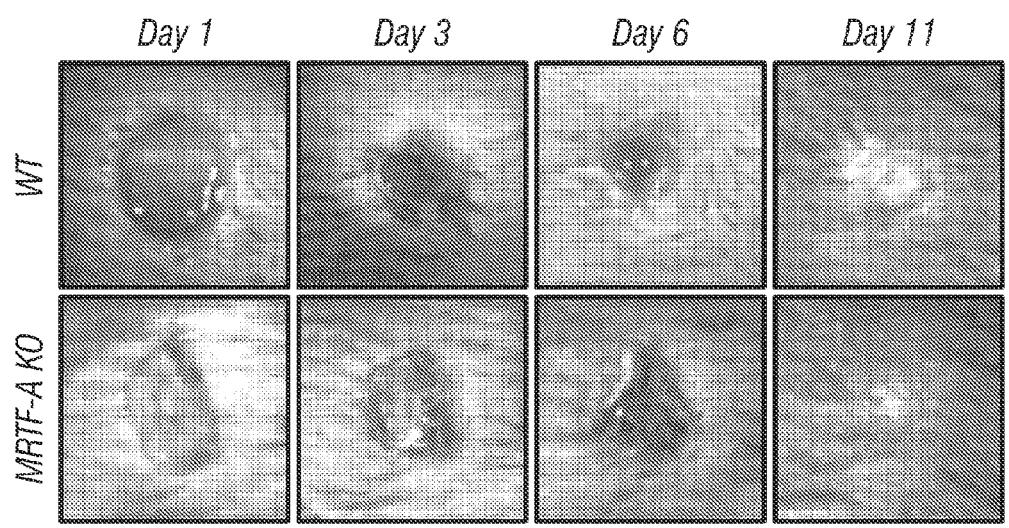
FIGS. 13A-C. Cutaneous wound healing in MRTF-A-null mice.
Figure 13B:
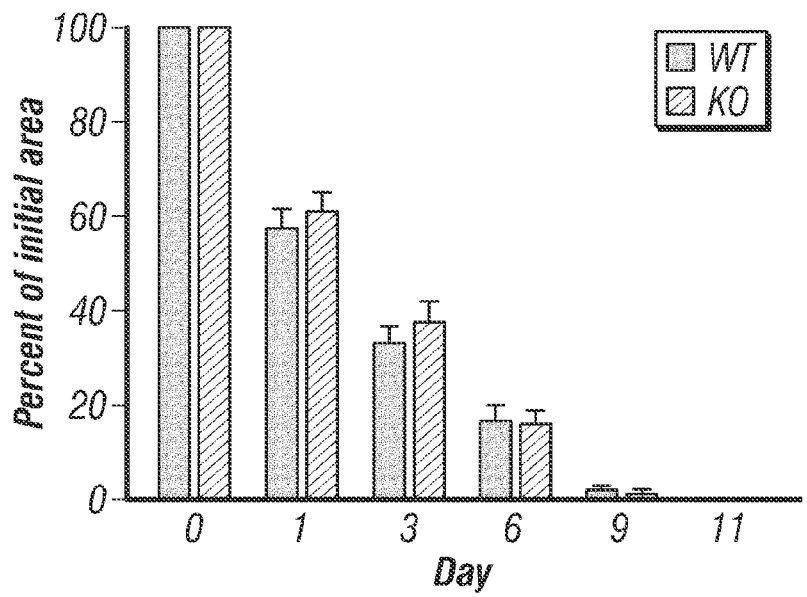
Figure 13C:
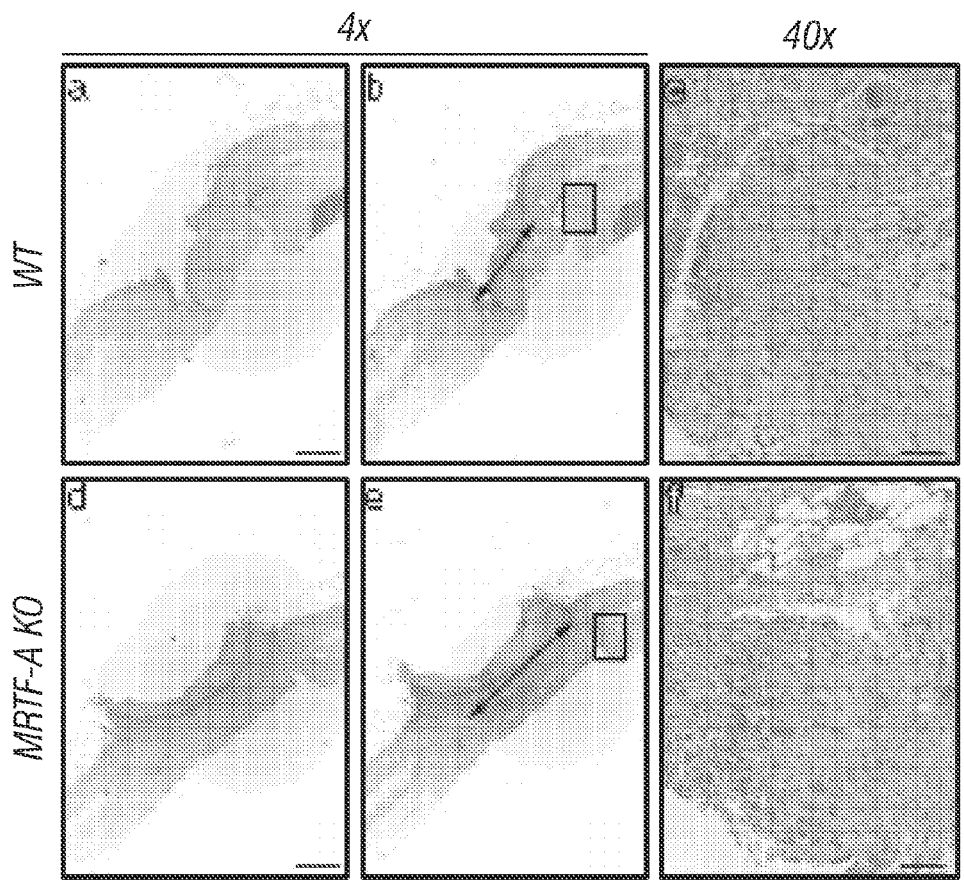
Figure 14:
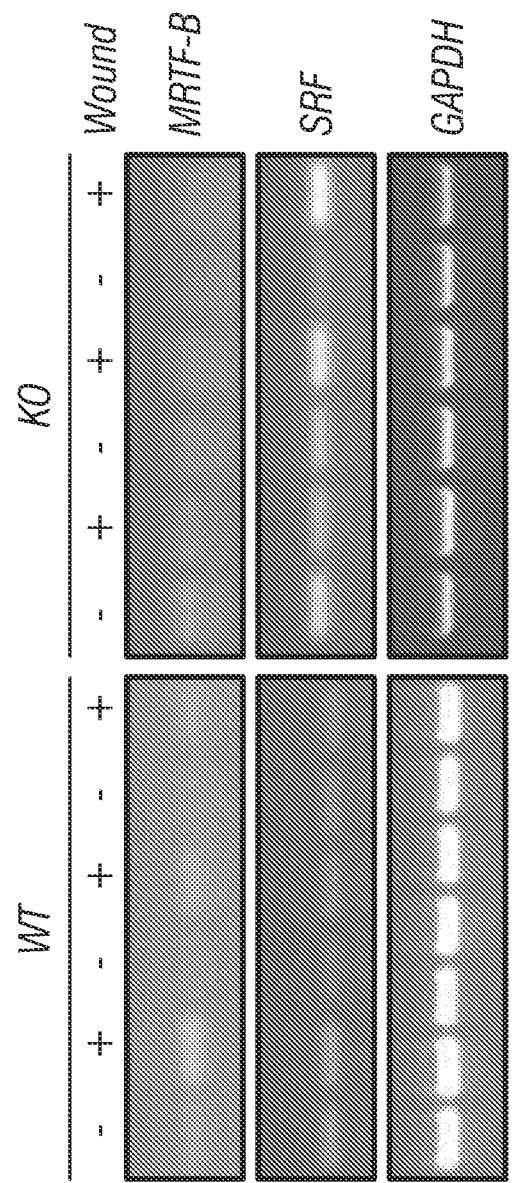
FIG. 14. SRF and MRTF-B expression in wounds from WT and MRTF-A KO mice. Gene expression was examined by RT-PCR from biopsies taken from fullthickness cutaneous wounds or control unwounded skin, 7 d after injury in mice. Expression levels were examined for three independent mice per genotype, using GAPDH as loading control. (−) denotes control unwounded skin; (+) denotes wound tissue.

A mouse model of cutaneous wound healing was used in this study as a means of testing the therapeutic efficacy of promoting myofibroblast differentiation with isoxazole in vivo. Isoxazole treatment increased the accumulation of granulation tissue and stimulated wound closure after seven days. If the beneficial effect of isoxazole was primarily due to MRTF-A activation, MRTF-A KO mice would be expected to display deficient wound closure. Surprisingly, however, MRTF-A deletion did not significantly impact wound healing over the course of eleven days (FIGS. 13A-C). The inventors postulate that MRTF-B, which is expressed in the wounds of MRTF-A null mice (FIG. 14), plays a redundant role to that of MRTF-A either in fibroblasts or keratinocytes. Indeed, SRF-deficient keratinocytes display reduced cell-cell and cell-matrix contacts and loss of epidermal homeostasis (Koegel et al., 2009). Isoxazole may also act independently of MRTF-A in the setting of a healing wound such that stimulation of Erk1/2 signaling by isoxazole contributes to wound closure by promoting the growth response. Alternatively, suppression of the inflammatory response, as demonstrated by reduced TNF-α expression, might contribute to the accumulation of granulation tissue in the isoxazole-treated wound (Desmouliere et al., 1992 and Liu et al., 2009). To fully elucidate the role of MRTFs in wound healing, deletion of MRTF-A and -B with both fibroblast and keratinocyte specific Cre drivers will likely be necessary.

Fibroblast activation is invariably associated with the healing process, contributing to injury repair in settings as diverse as cutaneous wound healing, heart disease, renal obstruction, pulmonary and liver fibrosis, and scleroderma (Hinz 2007 and Tomasek et al., 2002). Therefore, insight gained using one model of tissue remodeling is likely to be applicable to a wide range of pathologies that are associated with inappropriate myofibroblast differentiation. One example of excessive fibroblast differentiation is keloid formation, a type of benign, but sometimes debilitating, fibrotic tumor that expands following injury. Keloid formation and the MRTF-SRF axis are both promoted by mechanical tension and focal adhesion kinase (FAK) (Wang et al., 2006), potentially linking MRTFs to abnormal scar formation. The current finding of an MRTF-regulated pathway in dermal myofibroblast differentiation suggests potential therapeutic strategies directed towards various fibrotic diseases including keloid formation.

All of the compositions and methods disclosed and claimed herein can be made and executed without undue experimentation in light of the present disclosure. While the compositions and methods of this disclosure have been described in terms of particular embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

X. REFERENCES

The following references, to the extent that they provide exemplary procedural or other details supplementary to those set forth herein, are specifically incorporated herein by reference.

Akhmetshina et al., *Arthritis Rheum.*, 58:2553-2564, 2008.
Cao et al., *Mol Cell Biol*, 25(1):364-376, 2005.
Cen et al., *J Cell Biochem*, 93(1):74-82 2004.
Cogan et al., *J Biol Chem*, 277(39):36433-36442, 2002.
Cook et al., *Cell*, 27:487-496, 1981.
Davis et al., *In Vivo Dev Cell*, 2012.
Desmouliere et al., *Exp Cell Res*, 201(1):64-73, 1992.
Dioufa et al., *Proc Natl Acad Sci USA* 107(43):18611-18615, 2010.

Dioum et al., *Proc Natl Acad Sci USA*, 108(51):20713-20718, 2011.
Du et al., *Mol Cell Biol*, 23(7):2425-2437, 2003.
Elbashir et al., *Nature*, 411(6836):494-498, 2001.
Elberg et al., *Am J Physiol Renal Physiol*, 294(5):F1116-1128, 2008.
Eyden, *J Cell Mol Med*, 12(1):22-37, 2008.
Fan et al., *Mol Biol Cell*, 18(3):1083-1097, 2007.
Fire et al., *Nature*, 391:806-811, 1998.
Forster and Symons, *Cell*, 49:211-220, 1987.
Fu et al., *J Am. Soc. Nephrol.*, 17:3105-3114, 2006.
Fukushima et al., *Uver Int.*, 25:829-838, 2005.
Gerlach et al., *Nature* (London), 328:802-805, 1987.
Ghosh and Bachhawat, In: Liver Diseases, Targeted Diagnosis and Therapy Using Specific Receptors and Ligands, Wu et al. (Eds.), Marcel Dekker, NY, 87-104, 1991.
Greene et al., *Immunology Today*, 10:272, 1989
Grinnell & Petroll, *Annu Rev Cell Dev Biol*, 26:335-361, 2010.
Grishok et al., *Science*, 287:2494-2497, 2000.
Guettler et al., *Mol Cell Biol*, 28(2):732-742, 2008.
Guettler et al., *Mol Cell Biol*, 28:732-742, 2008.
Gurtner et al., *Nature*, 453(7193):314-321, 2008.
Hamid et al., *Am. J. Physiol. Heart Circ. Physiol.*, 292: H2598-H2606, 2007.
Hattori et al., *Circulation*, 109:2234-2239, 2004.
Haudek et al., *Cardiovasc Res.*, 83:511-518, 2009.
Hautmann et al., *J Biol Chem*, 272(16):10948-10956, 1997.
Hinz et al., *Mol Biol Cell*, 12(9):2730-2741, 2001
Hinz, *J Invest Dermatol*, 127(3):526-537, 2007.
Hoofnagle et al., *Am J Physiol Heart Circ Physiol*, 300(5): H1707-1721, 2011.
Huang et al., *J Clin Invest*, 122 (10):3678-3691, 2012.
Ketting et al., *Cell*, 99:133-141, 1999.
Kim and Cook, *Proc. Natl. Acad. Sci. USA*, 84:8788-8792, 1987.
Koegel et al., *J Clin Invest*, 119(4):899-910, 2009.
Krlitzfeldt et al., *Nature*, 438(7068):685-9, 2005.
Kuwahara et al., *J. Clin. Invest.*, 117:1324-1334, 2007.
Kuwahara et al., *Mol. Cell Biol.*, 25:3173-3181, 2005.
Kuwahara et al., *Mol Cell Biol*, 25(8):3173-3181, 2005.
Laspia et al., *Cell*, 59:283, 1989.
Latimer et al., *Mol. Cell. Biol.*, 10:760, 1990.
Li et al., *Mol Cell Biol* 26(15):5797-5808, 2006.
Li et al., *J. Biol. Chem.*, 271:19402-8, 1996.
Li et al., *Mol. Cell Biol.*, 26:5797-5808, 2006.
Li et al., *Proc. Natl. Acad. Sci. USA*, 100(16):9366-9370, 2003.
Li et al., *Proc. Natl. Acad. Sci. USA*, 100:9366-9370, 2003.
Lin and Avery, *Nature*, 402:128-129, 1999.
Lin et al., *Mol. Cell. Biol.*, 10:850, 1990.
Liu et al., *Mol Biol Cell*, 20(8):2174-2185, 2009.
Mack et al., *J. Biol. Chem.*, 276:341-347, 2001.
Majors and Varmus, *Proc. Natl. Acad. Sci. USA*, 80:5866, 1983.
Miano, *J. Mol. Cell Cardiol.*, 35:577-593, 2003.
Michel and Westhof, *J. Mol. Biol.*, 216:585-610, 1990.
Miralles et al., *Cell* 113(3):329-342, 2003.
Montgomery et al., *Proc. Natl. Acad. Sci. USA*, 95:155-215507, 1998.
Moss et al., *J. Gen. Physiol.*, 108(6):473-84, 1996.
Muehlich et al., *Mol Cell Biol*, 28(20):6302-6313, 2008.
Oh et al., *Proc. Natl. Acad. Sci. USA*, 102:15122-15127, 2005.
Olson & Nordheim, *Nat Rev Mol Cell Biol*, 11(5):353-365, 2010.
PCT Appln. WO 00/44914
PCT Appln. WO 01/36646
PCT Appln. WO 01/68836
PCT Appln. WO 99/32619
Philippar et al., *Mol. Cell*, 16:867-880, 2004.
Pipes et al., *Genes Dev.*, 20:1545 1556, 2006.
Pipes, *Genes Dev.*, 20(12):1545-1556, 2006.
Qiu et al., *Circ. Res.*, 97:983-991, 2005.
Qiu et al., *J Mol. Cell Cardiol.*, 35:1407-1420, 2003.
Reinhold-Hurek and Shub, *Nature*, 357:173-176, 1992.
Rhee et al., *Proc Natl Acad Sci USA* 104(13):5425-5430, 2007.
Rikitake et al., *Circulation*, 112:2959-2965, 2005.
Roux et al., *Proc. Natl. Acad. Sci. USA*, 86:9079-9083, 1989.
Russell et al., *ACS Chemical Biology*, 7(6):1067-1076, 2012.
Russell et al., *ACS Chemical Biology*, 7(6):1077-1083, 2012.
Sarver et al., *Science*, 247:1222-1225, 1990.
Satake et al., *J Virology*, 62:970, 1988.
Scanlon et al., *Proc. Natl. Acad. Sci. USA*, 88:10591-10595, 1991.
Schaffner et al., *J Mol. Biol.*, 201:81, 1988.
Schneider, et al., *Nat Chem Biol*, 4(7):408-410, 2008.
Sharp, *Genes Dev.*, 13:139-141, 1999.
Shaw et al., *Cell*, 56(4):563-572, 1989.
Sherman et al., *Mol. Cell. Biol.*, 9:50, 1989.
Sleigh and Lockett, *EMBO J.*, 4:3831, 1985.
Small et al., *Circ Res*, 107(2):294-304, 2010.
Small et al., *Development*, 132(5):987-997, 2005.
Small, *J Cardiovasular Trans Res*, 5(6):794-804, 2012.
Song et al., *Nature*, 485(7400):599-604, 2012.
Subramanian et al., *Mol Biol Cell*, 15(10):4532-4543, 2004.
Sun et al. *Genome Res*, 16(2):197-207, 2006.
Tabara et al., *Cell*, 99:123-132, 1999.
Tomasek et al., *Am J Pathol*, 166(5):1343-1351, 2005.
Tomasek et al., *Nat Rev Mol Cell Biol*, 3(5):349-363, 2002.
U.S. Pat. No. 4,458,066
U.S. Pat. No. 5,354,855
U.S. Pat. No. 5,795,715
U.S. Pat. No. 5,889,136
Varmus et al., *Cell*, 25:23-36, 1981.
Wang and Calame, *Cell*, 47:241, 1986.
Wang et al, *Proc Natl Acad Sci USA*, 99(23):14855-14860, 2002.
Wang et al., *Cell*, 105(7):851-862, 2001.
Wang et al., *Cell*, 105:851-862, 2001.
Wang et al., *J Cell Physiol*, 206(2):510-517, 2006.
Wang et al., *Nature*, 428(6979):185-189, 2004.
Wang et al., *Proc. Natl. Acad. Sci. USA*, 100:7129-7134, 2003.
Wang et al., *Proc. Natl. Acad. Sci. USA*, 99:14855-14860, 2002.
Wincott et al., *Nucleic Acids Res.*, 23(14):2677-2684, 1995.
Wynn, *J Pathol*, 214(2):199-210, 2008.
Zhang et al., *FASEB J.*, 20:916-925, 2006.
Zhao et al., *J Cell Sci*, 120(Pt 10):1801-1809, 2007.

What is claimed:

1. A method of treating a wound in a subject comprising contacting said wound with a composition comprising an isoxazole having the formula:

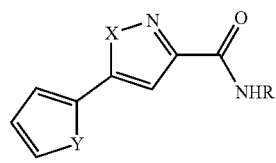

wherein X is O, Y is S or O and R is H, a substituted or unsubstituted alkyl, substituted or unsubstituted alkenyl, a substituted or unsubstituted alkynyl, or a stereoisomer, solvate, hydrate, or pharmaceutically acceptable salt thereof.

2. The method of claim 1, wherein said wound is a dermal wound, and epidermal wound, a burn, a laceration or abrasion, an infectious lesion, a surgical site, an ulcer a puncture, a chronic wound, a scar, keloid or a blister.

3. The method of claim 1, wherein the isoxazole is contacted with said wound in a wound dressing, a suture, a gel, a salve, an ointment, a topical spray, a powder, a topical liquid or by injection.

4. The method of claim 1, further comprising providing to said subject a second wound therapy.

5. The method of claim 4, wherein said second wound therapy is hyperbaric oxygen therapy (HBO), negative pressure therapy (VAC), electrical stimulation, phototherapy, acoustic stimulation, a corticosteroid, a cytotoxic drug, an antibiotic, an antiseptic, nicotine, an anti-platelet drug, an NSAID, colchicine, an anti-coagulant, a vasoconstricting drug or an immunosuppressive, a growth factor, an antibody, a protease, a protease inhibitor, an antibacterial peptide, an adhesive peptide, a hemostatic agent, living cells, honey, or nitric oxide.

6. The method of claim 1, wherein said subject is a human or a non-human mammal.

7. A device for the treatment of a wound in a subject comprising:
(a) a composition comprising an isoxazole having the formula:

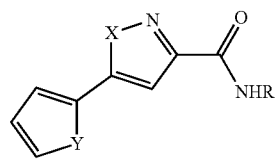

wherein X is O, Y is S or O and R is H, a substituted or unsubstituted alkyl, substituted or unsubstituted alkenyl, a substituted or unsubstituted alkynyl, or a stereoisomer, solvate, hydrate, or pharmaceutically acceptable salt thereof;
(b) a sterile dressing into or onto which the isoxazole, stereoisomer, solvate, hydrate, or pharmaceutically acceptable salt thereof is disposed.

8. The device of claim 7, wherein said sterile dressing is a film, foam, semi-solid gel, pad, gauze, fabric.

9. The device of claim 7, wherein said sterile dressing is a silicone dressing, a fibrin/fibrinogen dressing, a polyacrylamide dressing, a PTFE dressing, a PGA dressing, a PLA dressing, a PLGA dressing, a polycaprolactone dressing or a hyaluronic acid dressing.

10. The device of claim 7, wherein said sterile dressing further comprises gelatin, silver, cellulose, an alginate, collagen, a hydrocolloid, a hydrogel, a skin substitute, a wound filler, a growth factor, an antibody, a protease, a protease inhibitor, an antibacterial peptide, an adhesive peptide, a hemostatic agent, living cells, honey, or nitric oxide.

11. The device of claim 7, further comprising a substance or element for the fixation of said device to a wound.

12. The device of claim 7, wherein said substance is an adhesive or a bandage.

13. The device of claim 7, wherein said device further comprises one or more of a lubricant, an absorber, a sponge, a wound veil, an odor control agent, and/or a cover.

14. The device of claim 7, wherein the isoxazole, salt or analog is contained in a liquid, salve, ointment, gel or powder disposed in or on said sterile dressing.

15. The device of claim 7, wherein said sterile dressing further comprises one or more of a corticosteroid, a cytotoxic drug, an antibiotic, an antimicrobial, an antifungal, an antiseptic, nicotine, an anti-platelet drug, an NSAID, colchicine, an anti-coagulant, a vasoconstricting drug or an immunosuppressive.

16. The device of claim 7, further comprising a port providing operable connection between said sterile dressing and a tube, and/or a cover providing for an airtight seal to or around a would surface.

17. The device of claim 16, further comprising a drainage tube operably connected to said port at one end and suitable for attachment to a negative pressure device at another end.

18. The device of claim 16, wherein said sterile dressing is gauze or foam.

19. A method of promoting wound repair in a subject comprising contacting said wound with a device according to claim 7.

20. A suture comprising an isoxazole impregnated into or disposed thereon, wherein the isoxazole has the formula:

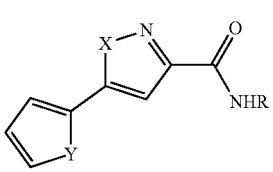

wherein X is O, Y is S or O and R is H, a substituted or unsubstituted alkyl, substituted or unsubstituted alkenyl, a substituted or unsubstituted alkynyl, or a stereoisomer, solvate, hydrate, or pharmaceutically acceptable salt thereof.

21. The method of claim 1, wherein R is $C_1$-$C_6$ alkyl, $C_3$-$C_6$ cycloalkyl, $C_2$-$C_6$ alkenyl, or $C_2$-$C_6$ alkynyl.

22. The method of claim 1, wherein Y is S.

23. The device of claim 7, wherein R is $C_1$-$C_6$ alkyl, $C_3$-$C_6$ cycloalkyl, $C_2$-$C_6$ alkenyl, or $C_2$-$C_6$ alkynyl.

24. The device of claim 7, wherein Y is S.

25. The method of claim 19, wherein R is $C_1$-$C_6$ alkyl, $C_3$-$C_6$ cycloalkyl, $C_2$-$C_6$ alkenyl, or $C_2$-$C_6$ alkynyl.

26. The method of claim 19, wherein Y is S.

27. The suture of claim 20, wherein R is $C_1$-$C_6$ alkyl, $C_3$-$C_6$ cycloalkyl, $C_2$-$C_6$ alkenyl, or $C_2$-$C_6$ alkynyl.

28. The suture of claim 20, wherein Y is S.

* * * * *